(12) United States Patent
Benns et al.

(10) Patent No.: US 10,046,150 B2
(45) Date of Patent: Aug. 14, 2018

(54) LYSINE DELIVERY SYSTEMS FOR BLOOD COAGULATION

(71) Applicant: Park City Bio, LLC, Park City, UT (US)

(72) Inventors: Jonathan M. Benns, Salt Lake City, UT (US); Matthew C. Lawyer, Park City, UT (US)

(73) Assignee: Park City Bio, LLC, Park City, UT (US)

( * ) Notice: Subject to any disclaimer, the term of this patent is extended or adjusted under 35 U.S.C. 154(b) by 0 days.

(21) Appl. No.: 15/697,072

(22) Filed: Sep. 6, 2017

(65) Prior Publication Data

US 2017/0361075 A1    Dec. 21, 2017

Related U.S. Application Data

(62) Division of application No. 14/268,639, filed on May 2, 2014, now Pat. No. 9,757,547.

(60) Provisional application No. 61/819,021, filed on May 3, 2013.

(51) Int. Cl.
*A61K 38/36* (2006.01)
*A61K 31/198* (2006.01)
*A61M 31/00* (2006.01)

(52) U.S. Cl.
CPC ......... *A61M 31/002* (2013.01); *A61K 31/198* (2013.01)

(58) Field of Classification Search
None
See application file for complete search history.

(56) References Cited

U.S. PATENT DOCUMENTS

| 4,778,679 | A | 10/1988 | Silvetti |
| 5,510,102 | A | 4/1996 | Cochrum |
| 2011/0311660 | A1 | 12/2011 | Dockter |
| 2013/0095165 | A1* | 4/2013 | Olson ............... A61L 15/44 424/443 |
| 2013/0345678 | A1 | 12/2013 | Rubin |

FOREIGN PATENT DOCUMENTS

| AU | 2009100610 | 6/2009 |
| CN | 202608338 U | 12/2012 |

OTHER PUBLICATIONS

Collen, D., "Natural inhibitors of fibrinolysis", J Clin Pathol, 33, Suppl (Roy Coll Path), 14, pp. 24-30.
Rath, Matthias et al.,"Plasmin-Induced Proteolysis and the Role of Apoprotein(a), Lysine, and Synthetic Lysine Analogs", Journal of Orthomolecular Medicine, 1992, vol. 7, No. 1, pp. 17-23.

* cited by examiner

*Primary Examiner* — Robert T. Crow
*Assistant Examiner* — John P Nguyen
(74) *Attorney, Agent, or Firm* — Maschoff Brennan

(57) ABSTRACT

A blood coagulating device can include an absorbent body; and a hemostatic lysine composition associated with the body. The body can have a cylindrical or conical member having a first end having the hemostatic composition, the first end being configured for insertion into a nasal passageway. A method for coagulating blood can include providing a powdered hemostatic lysine composition; and applying the powdered hemostatic lysine composition to blood so as to cause the blood to coagulate and form a clot. The coagulation can occur in a nasal passageway away from a blood vessel. The method can include providing at least one absorbent member having the powdered hemostatic lysine composition; and applying the at least one absorbent member to the blood so that the powdered hemostatic lysine composition causes the blood to coagulate and clot.

20 Claims, 22 Drawing Sheets

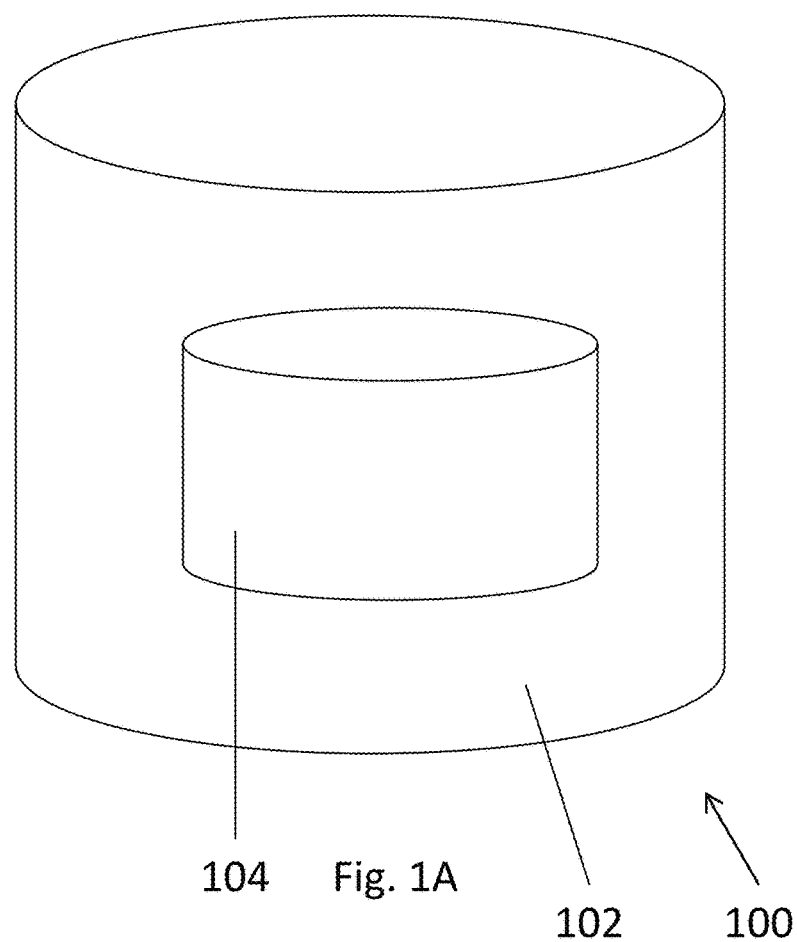
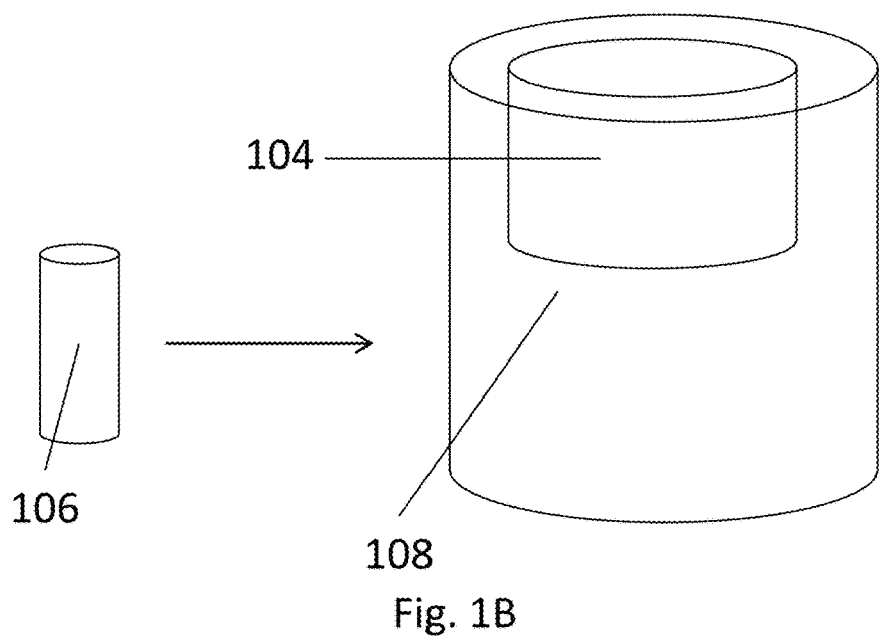

110   112   Fig. 1C 132
130

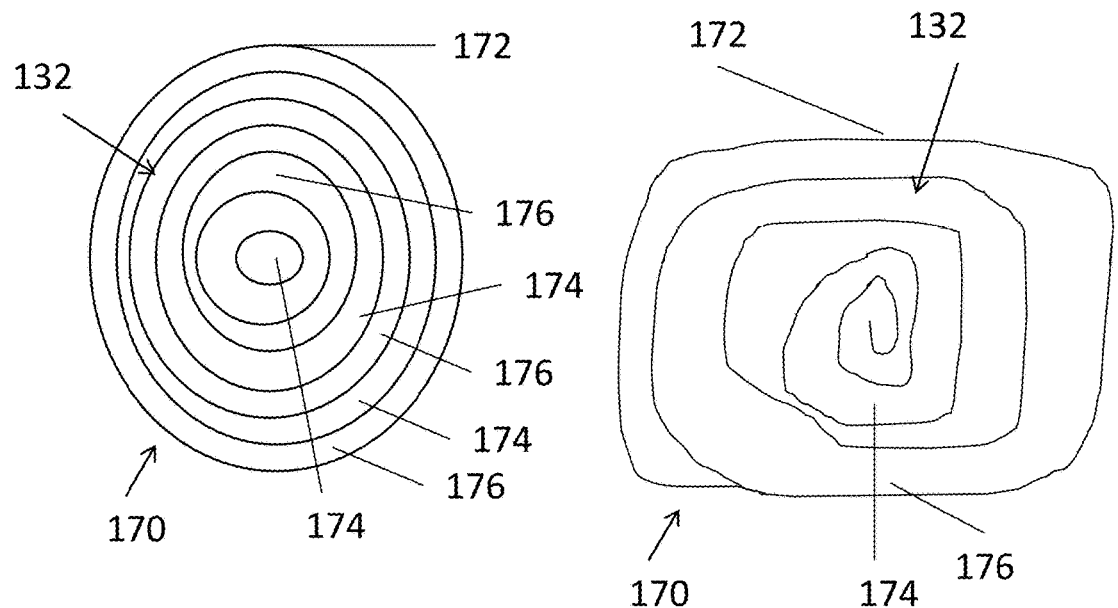
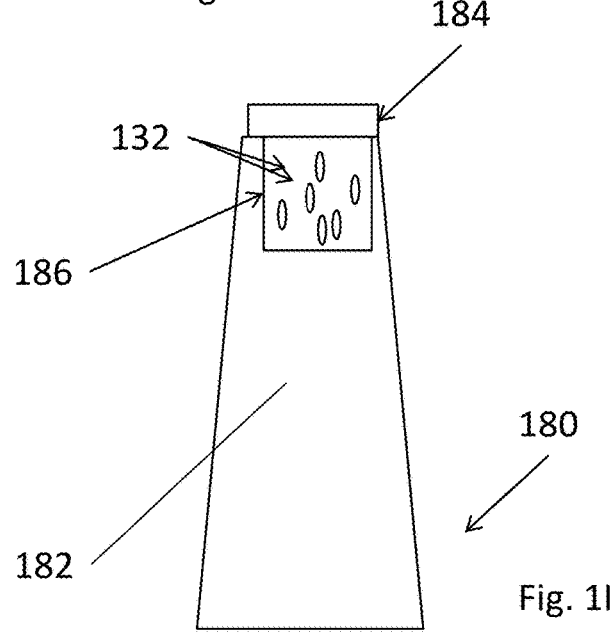
Fig. 1H
Fig. 1I

Fig. 8
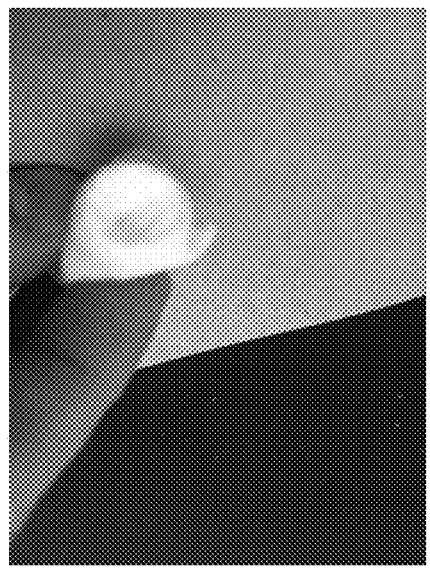 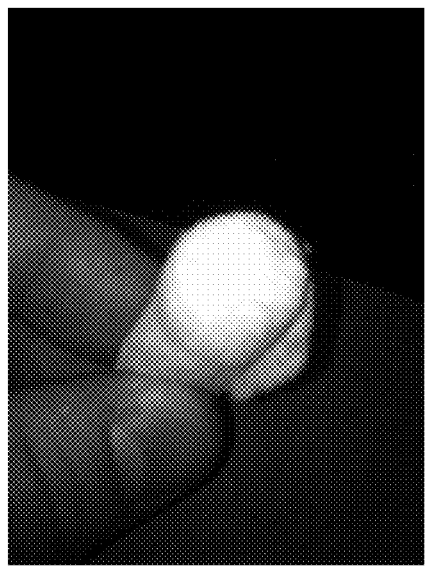
Fig. 9A          Fig. 9B

LYSINE DELIVERY SYSTEMS FOR BLOOD COAGULATION

CROSS REFERENCE

This patent application is a divisional application of U.S. Ser. No. 14/268,639 filed May 2, 2014, which claims benefit of U.S. Provisional 61/819,021 filed May 3, 2013, which applications are both incorporated in herein by specific reference in their entirety.

BACKGROUND

Generally, coagulation (i.e., thrombogenesis) is the process by which blood changes from being flowable to forming clots. Coagulation is an important part of hemostasis, which is the cessation of blood loss from a damaged vessel, wherein a damaged blood vessel wall is covered by a platelet and fibrin-containing clot to stop bleeding and begin repair of the damaged vessel. Disorders of coagulation can lead to an increased risk of bleeding (hemorrhage) or obstructive clotting (thrombosis). Coagulation is highly conserved throughout biology; in all mammals, coagulation involves both a cellular (platelet) and a protein (coagulation factor) component. Coagulation begins almost instantly after an injury to the blood vessel has damaged the endothelium lining the vessel. Blood begins to coagulate upon exposure to air. Also, exposure of the blood to proteins, such as tissue factor, initiates changes to blood platelets and the plasma protein fibrinogen, a clotting factor. Platelets immediately begin to form a plug at the site of injury, which is called primary hemostasis. Secondary hemostasis occurs simultaneously where proteins in the blood plasma, called coagulation factors or clotting factors, respond in a complex cascade to form fibrin strands, which thicken the blood strengthen the platelet plug.

It is apparent that the balance between flowable blood and coagulating blood is tenuous. As such, tipping the balance from flowable blood to coagulating blood can be beneficial in a number of instances. For example, when a blood vessel becomes compromised so that there is an opening allowing blood to escape, the body signals for the initiation of the events to coagulate the blood and repair the vessel. Therefore, it can be advantageous to have systems and methods that promote blood coagulation. However, it is difficult to determine which pathway can be inhibited for promoting effective blood coagulation in particular circumstances.

BRIEF DESCRIPTION OF FIGURES

FIGS. 1A-1K illustrate embodiments of devices having hemostatic compositions.

FIG. 8 is an image that shows a lysine tissue with the lysine powder being in a receptacle at the end that is inserted in the nostril, where the blood adsorbs into the tissue and the lysine powder remaining white after use, which indicates the lysine causes the blood to coagulate and form a barrier so that the lysine that has not touched the blood remains in the tissue and receptacle.

FIG. 9A is an image that shows a rolled tissue device having a receptacle at the end empty.

FIG. 9B is an image that shows the receptacle filled with lysine powder.

DETAILED DESCRIPTION

Figure 1D:
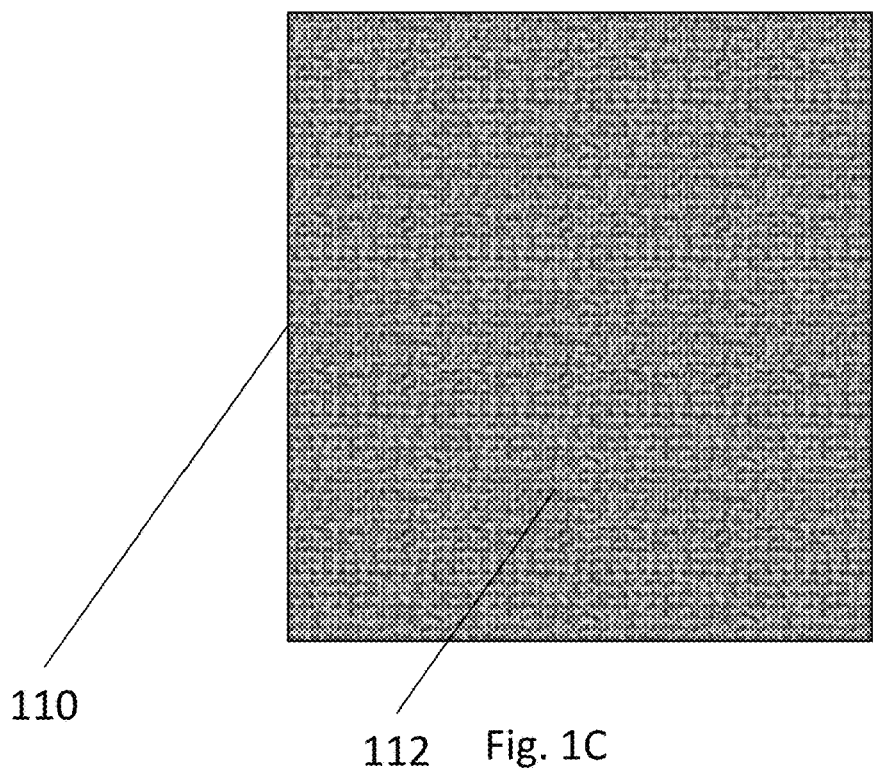
Figure 1D:
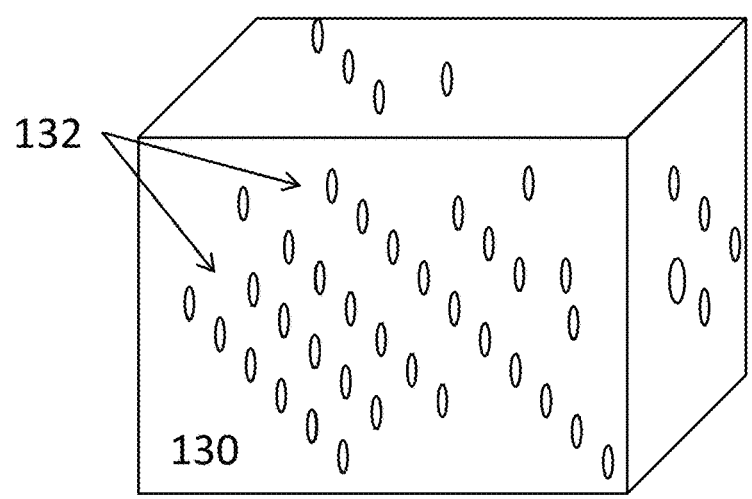

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In one embodiment, the present invention provides a hemostatic composition for coagulating blood. The hemostatic composition includes: a lysine or derivative thereof in an amount sufficient to coagulate blood, optionally in a nasal passageway, wound, surgical site, or vagina. The hemostatic composition can be formulated with the lysine being selected from L-lysine, D-lysine, poly(L-lysine), poly(D-lysine), poly(L,D-lysine), alpha lysine, beta lysine, or combination or derivative thereof. The hemostatic composition can include a lysine derivative that is selected from tranexamic acid, aminocaproic acid, and combination thereof. The lysine derivative may include an alkyl chain in the side group from C1-C20, from C4-C15, or from C5-C10. In one aspect, the lysine derivative includes the alkyl chain of the side group being longer than lysine. The lysine or derivative can include Formula 1, where n is from 0-20, 1-15, 1-10, or 1-5, or 1. However, in one aspect, the invention uses lysine and not a lysine derivative.

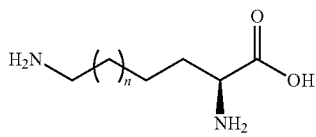

The hemostatic composition can be in any format ranging from solids to liquids to gases or the like. However, examples of formats for the hemostatic composition can include a powder having a plurality of lysine-containing particles. The particles can be stuck together by lysine agglomeration, or another agent can be used to form the particles. The particles can be flowable or in a matrix, such as a polymeric matrix. The particles can be pure lysine, or lysine combined with a carrier or other agents. The particles can be of various sizes, and a hemostatic composition can have different particle sizes also. The hemostatic composition may include single lysine molecules together without being physically agglomerated. The particles can range from 100 Angstroms to 1 mm, for example, or 500 Angstroms to 500 microns, 1 nanometer to 100 microns, 100 nanometers to 1 micron, 500 nanometers to 750 nanometers.

The lysine particles or powder can be pressed into various shapes. The pressed particles can include formulating agents that enhance the shape to be retained and to be blood absorbent. In one example, the hemostatic composition is a compressed sheet. In one example, the hemostatic composition is molded into any moldable shape. In one example, the hemostatic composition is molded into an elongate cylindrical member, spherical member, complex shape, squared shape, polygonal shape, rounded shape, tapered shape, or other. In one example, the hemostatic composition is granular. In one example, the hemostatic composition includes a microparticle having the lysine. In one example, the hemostatic composition includes a nanoparticle having the lysine. The nanoparticle and/or microparticle can be polymeric, and prepared from a biocompatible polymer, which may or may not be biodegradable.

The hemostatic composition can be formulated to be pure lysine or include lysine as the only coagulation-inducing molecule. However, the hemostatic composition can include another active agent. The other agent may or may not be another coagulating or hemostatic substance, such as those described herein or generally known.

The lysine or lysine derivative can be included in the hemostatic composition at various amounts. Accordingly, the lysine or lysine derivative can be present in the hemostatic composition in an effective amount to inhibit plasminogen. The lysine or lysine derivative can be present in an effective amount to inhibit plasminogen conversion to plasmin. The lysine or lysine derivative can be present in an effective amount to inhibit formation of plasmin. The lysine or lysine derivative can be present in an effective amount to inhibit fibrinolysis. The lysine or lysine derivative can be present in an effective amount to occupy a lysine binding site on plasminogen so inhibit conversion to plasmin. The lysine or lysine derivative can be present in an effective amount to occupy a lysine binding site in a Kringle domain on plasminogen so inhibit conversion to plasmin. These effective amounts can be sufficient to induce coagulation, or cause blood to thicken and have reduced flow or to clot or otherwise stop bleeding. For example, the lysine or lysine derivative can be present in an effective amount to cause blood coagulation on a nasal membrane.

The hemostatic composition can be formulated as is generally known in the art of nutraceutical or pharmaceutical formulations. The hemostatic composition can include one or more of excipients, adjuvant, lubricants, pharmaceutically acceptable carrier, flavorant, odorant, absorbent, or the like. For example, the hemostatic composition can include stearic acid and/or magnesium stearate.

In one embodiment, the hemostatic composition is devoid of another active agent besides lysine or lysine derivative. Also, the hemostatic composition can include lysine but be devoid of at least one of tranexamic acid and aminocaproic acid or devoid of both. The hemostatic composition can consist of lysine as a hemostatic, such as a lysine powder. However, the powder may include other substances but without a lysine derivative (e.g., tranexamic acid and aminocaproic acid).

The hemostatic composition of the present invention can have a lot of delivery protocols to administer lysine, such that the lysine causes blood coagulation. In one example, the hemostatic composition can be located in a nasal passageway, wound, surgical site, or vagina. The hemostatic composition may be located on a mucosal membrane in the nasal passageway or other. For nasal delivery, the hemostatic composition can be provided or sprayed into an aerosolized powder format. The powder may be puffed into the nose so that it is in cloud or aerosol to apply a thin layer of lysine to the blood flowing in the nasal passageway in order to inhibit plasminogen conversion to plasmin, and thereby promote blood clotting along the blood flow. Application of the lysine to the mucus membranes that the blood later flows over can cause blood coagulation on contact to inhibit the blood flow. The delivery of lysine to blood and/or mucus membranes or other nasal passageway surfaces can promote blood coagulation to reduce or stop the flow of blood in the nasal passageway to inhibit blood from leaking out of the nose. The delivery of lysine or derivative thereof can be in a dry format, such as a powder. In one aspect, the present invention excludes the use of a wet or liquid having the lysine and/or lysine derivative.

The hemostatic composition of any of the embodiments described herein can be provided to include a plurality of lysine molecules in a powder reservoir or other dry format, preferably absorbent dry format. The powder reservoir can be in a container or other chamber that retains the lysine molecules together. The lysine molecules can be withdrawn, extracted, propelled, or otherwise removed from the powder reservoir during administration. The powder reservoir can be administered to blood to release lysine into the blood to initiate coagulation, or the lysine powder can be released from the reservoir into the blood. The lysine powder reservoir or dry lysine may be located in a medical device.

In one embodiment, a medical device includes the hemostatic composition of the present invention. The hemostatic composition can be coated onto a medical device, included in a reservoir or depot, or be absorbed into a matrix or other format. The medical device can be powdered with lysine or have an outer coating impregnated with lysine. The medical device can release the lysine upon administration. The site of administration can be a wound, bleeding nose, surgical site, or vagina. The medical device can provide the lysine locally to coagulate the blood locally, which can be beneficial during surgery or to slow the flow of blood, such as in a nose. The medical device can include any surgical equipment, sutures, catheters, implants, tissue scaffolds, or other.

The hemostatic composition of any of the embodiments may be located on or in an absorbent member. The absorbent member can be blood absorbent, where water absorbent members can be blood absorbent. The member can be solid or porous or have interstitial spaces to receive the blood. The member can have the lysine so that the lysine is provided to the blood so that the lysine absorbs into the blood. The lysine transfers from the absorbent member to the blood to promote coagulation to stop the flow of blood in the nasal passageway. The lysine contacting the blood can be absorbed through the flow in order to promote coagulation up into the nasal passageway. The lysine may be delivered to the bleeding vessel by the blood flow to promote coagulation at that site, and thereby be delivered to the flowing blood to stop the flow. As such, the coagulation of blood can be distal or away from an actively bleeding blood vessel. The coagulation can be in the nasal passageway or in the vagina. Also, the coagulation can be in or at a wound.

The hemostatic composition of any of the claims, the hemostatic composition is formed into a cylindrical member at a first end, the first end being configured for insertion into a nasal passageway. FIG. 1A shows a cylindrical member 100 that is adapted for insertion into a nostril. The cylindrical member 100 includes an outer member 102 and an internal lysine reservoir 104. While the cylindrical member appears round, it may be contoured to match nostril cross-sectional shapes. The outer member 102 can be an absorbent member forming a container with the lysine or lysine derivative located within the lysine reservoir 104 in the container.

FIG. 1B illustrates an embodiment of a hemostatic composition comprising a memory member. That is, the hemostatic composition has shape memory and can have a first shape in a relaxed state and then a second shape in a strained shape. The strained state 106 can fit into a nasal passageway, wound, surgical site, or other, and then the relaxed shape 108 can expand to contour to the environment such as the shape of the nasal passageway, wound, surgical site, or other. Accordingly, the hemostatic composition can include a memory member having a first compressed shape and a second expanded shape. The device can include the body being in a contracted form and having an expanded form upon contact with liquid, such as blood. The body can be blood-expandable from a first smaller size to a second larger size upon exposure to blood. The lysine reservoir 104 can be at an end of the device, which the end is inserted into a body cavity (e.g., nose or vagina) first.

In one embodiment, the hemostatic composition can include gauze. FIG. 1C shows the gauze 110 having the hemostatic composition 112. The gauze can be coated, powdered or otherwise externally applied with the lysine or derivative, or the gauze matrix can have the lysine absorbed therein. The lysine can be in a reservoir in the gauze 110. The lysine can be powdered onto the gauze and the powder can be in the interstitial spaces. The gauze can provide lysine over a large contact surface area. However, the hemostatic composition can include any carrier substrate having the lysine or lysine derivative. Preferably, the hemostatic composition is applied to or contained or embedded in a hemostatic carrier substrate. The hemostatic composition can include a mesh hemostatic carrier substrate having the lysine or lysine derivative.

The hemostatic composition can include a foam hemostatic carrier substrate having the lysine or lysine derivative. The foam can be an expandable foam, memory foam, set foam, rigid foam, malleable foam, or any other foam. Water-expandable foams or air expandable foams can be useful for sealing a passageway that is bleeding, such as a nostril. The foam can be compressed, then inserted into the nostril, then expanded to friction fit in the nostril. For example, a low pressure polyurethane sprayer can spray the foam into the nostril to seal the nostril and promote blood clotting. Other expandable foams can be used to carry the lysine.

The hemostatic composition can include any type of polymeric hemostatic carrier substrate having the lysine or lysine derivative. The polymer can be hemostatic or the polymer can contain a hemostatic agent. A hemostatic polymer can include cationic polymer such as polyethyleneamine, polylysine, or others. The hemostatic composition can include a comprising a cellulosic hemostatic carrier substrate having the lysine or lysine derivative. The cellulosic hemostatic carrier can include etherized oxidized regenerated cellulose, oxidized regenerated cellulose, chemically treated cellulose, ActCel, or others. The carrier may include a polysaccharide.

The hemostatic composition can include any tissue paper substrate having the lysine or lysine derivative. The tissue paper can be hygienic tissue paper, facial tissue, or other soft, absorbent, disposable paper that can be used in a nostril. The tissue can be impregnated with the lysine. The tissue can be folded or multiple sheets can be combined in order to form a tissue chamber having the lysine.

The hemostatic composition can include any nutraceutical composition combined with the lysine or lysine derivative. The nutraceutical composition can be beneficial for health or dietary supplement, such as isolated nutrients, herbal products, or the like.

The hemostatic composition can be devoid of a flowable liquid. As such, the hemostatic composition can be dry. The hemostatic composition can have no liquid or have a small amount such that the hemostatic composition can be considered to be dry. The hemostatic composition can be powdered and may include agglomerated particles. However, the hemostatic composition may be formulated as a gel, paste, or the like that can be smeared into a nostril, wound, surgical site, or other. The hemostatic composition can include microspheres or nanoparticles having the lysine contained therein.

The hemostatic composition can various amounts of the lysine or derivative, such a the hemostatic composition having less than 500 mg lysine or lysine derivative, less than 250 mg lysine or lysine derivative, having less than 100 mg lysine or lysine derivative, having less than 50 mg lysine or lysine derivative, having less than 25 mg lysine or lysine derivative, having less than 10 mg lysine or lysine derivative, having less than 5 mg lysine or lysine derivative, having less than 1 mg lysine or lysine derivative, having less than 0.5 mg lysine or lysine derivative, or alternatively having greater than 500 mg lysine or lysine derivative.

The hemostatic composition can be placed at various places on a subject in order to inhibit the blood from flowing outside of a blood vessel. The blood outside of the vessel can be inhibited from flowing by promoting blood coagulation. Also, the blood outside of the vessel can be inhibited from flowing by introducing lysine into the blood outside of the vessel. The lysine in the blood outside of the vessel can inhibit plasminogen from converting to plasmin. Accordingly, the lysine may saturate the plasminogen, and thereby be introduced into the blood outside of the vessel in a sufficient amount to saturate plasminogen at the lysine receptor so plasminogen remains in the closed position. The hemostatic composition can inhibit blood outside of the vessel from flowing or otherwise cause coagulation when located in a wound, internal would, skin wound, surgical site, nostril, vagina (e.g., during menstruation), or other. As such, a hemostatic composition of the invention can include blood outside of the vessel having the lysine in a coagulating amount or a plasminogen inhibiting amount. Accordingly, the coagulating or coagulated blood or a blood clot can include lysine obtained from the lysine hemostatic composition in an effective amount or amount described herein.

Figure 1E:
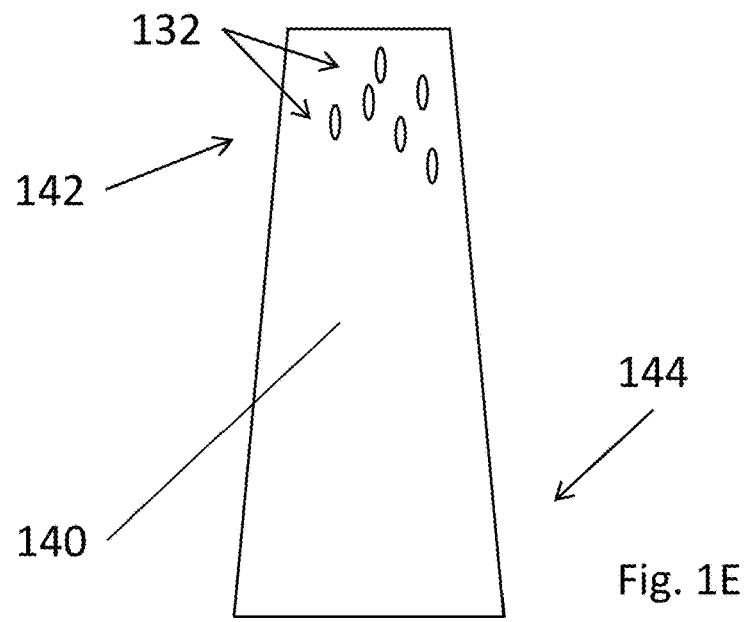

In one embodiment, the present invention includes a blood coagulating device. Such a blood coagulating device can include a body 130 and a hemostatic composition 132 of the invention associated with the body as shown in FIG. 1D. The body 130 comprising the hemostatic composition 132 embedded therein or located thereon. The hemostatic composition 132 can be any of the hemostatic compositions having the lysine or lysine derivative, and preferably only lysine as the coagulant devoid of a lysine derivative. The body 130 can include the body of any medical device, absorbent member, lysine delivery device, blister pack, burst pack, or other. The body can include a tapered cylindrical and/or conical member 140 having a first end 142 having the hemostatic composition 132, the first end 142 being configured for insertion into a nasal passageway as shown in FIG. 1E. The body 140 being tapered from one end (144) to an opposite end (e.g., first end 142).

Figure 1F:
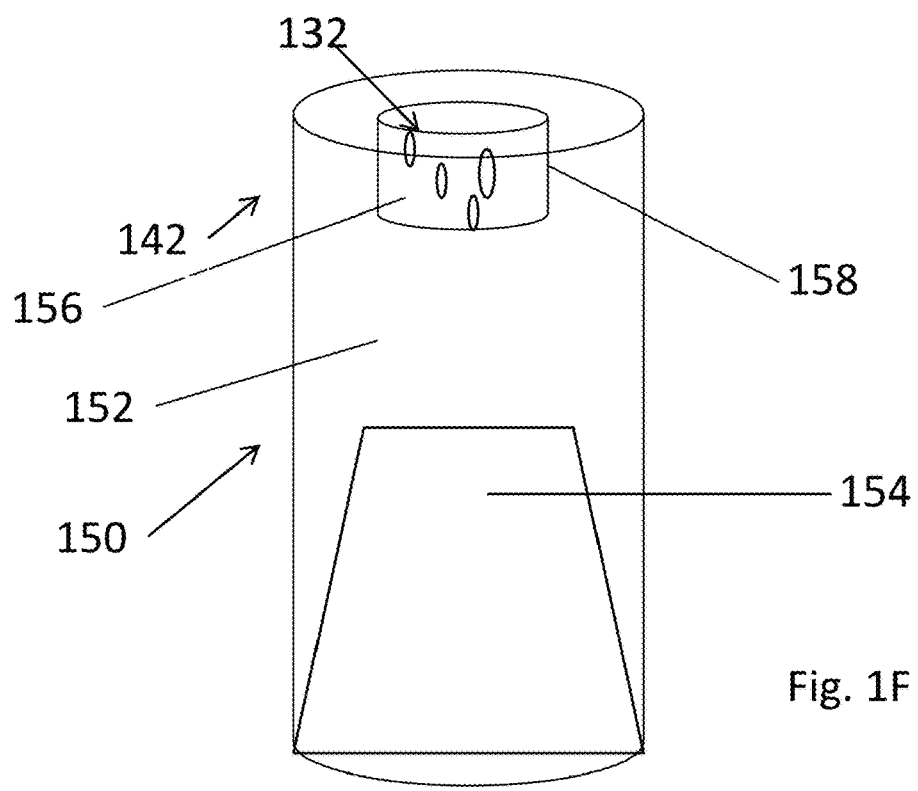

In one embodiment shown in FIG. 1F, the device 150 can include a body 152 that has a memory member 154 associated with the body 152. The memory member 154 can have a first compressed shape and a second expanded shape (e.g., FIG. 1B). The device 150 can include a first end 142 having a reservoir 156 having the hemostatic composition 132. The body 152 can have a memory member core 154 with an absorptive shell.

In one embodiment, the device can include a body of: gauze, a carrier substrate, a hemostatic carrier substrate; a mesh hemostatic carrier substrate, a foam hemostatic carrier substrate, a polymeric hemostatic carrier substrate, a cellulosic hemostatic carrier substrate, a tissue paper substrate having the lysine or lysine derivative, a polysaccharide or other. The hemostatic composition can be coated or embedded in or within interstitial spaces or in depots of the body.

In one embodiment, the body 152 can form a chamber (e.g. reservoir 156) with defined walls 158 that define the chamber. The chamber can contain the hemostatic composition 132 between the walls.

Figure 1G:
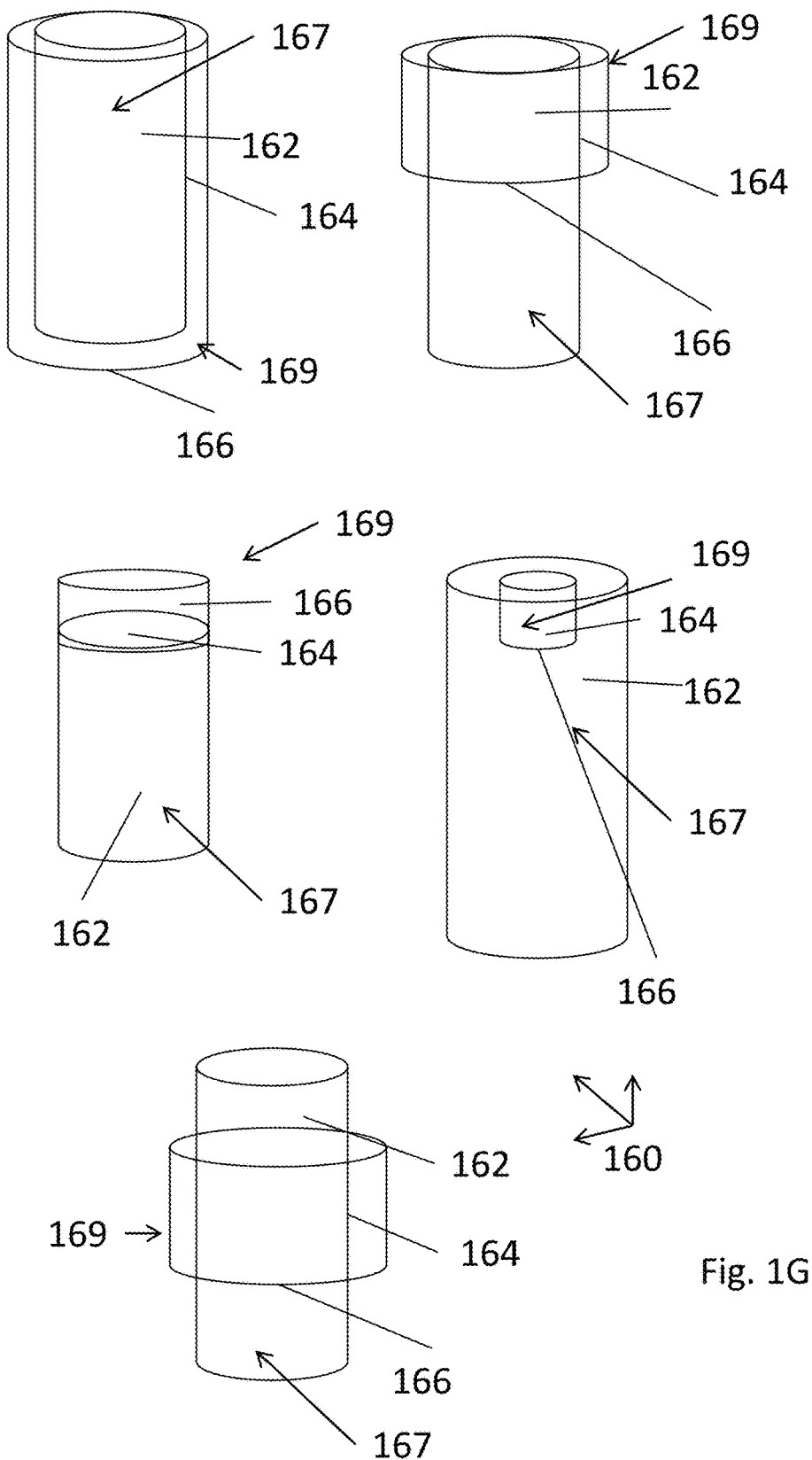

FIG. 1G shows different devices 160, each having a body 162 having a surface 164 with the hemostatic composition 166. This can include a body core 162 and a shell hemostatic composition 166 or a hemostatic composition core and body shell.

In one embodiment, the body of the device can have a blood-absorptive portion and a blood-non-absorptive portion, the hemostatic composition being associated with the blood-absorptive portion. For example, FIG. 1G can illustrate such a device 160 having a blood-absorptive portion 169 and a blood-non-absorptive portion 167. For example, the body 162 can be the non-absorptive portion 167 and the hemostatic composition 166 can be in a blood-absorptive portion 169. The device 160 can have a blood-non-absorptive portion 167 that includes a memory member and a blood-absorptive portion 169, the hemostatic composition 166 being associated with the blood-absorptive portion 169. The device 160 can have a blood-absorptive portion 169 and a blood-non-absorptive portion 167, the hemostatic composition 166 being associated with the blood-absorptive portion 169 and the blood-non-absorptive portion 167. The device 160 can have a blood-absorptive portion 169 and a blood-non-absorptive portion 167, the hemostatic composition 166 being between the blood-absorptive portion 169 and blood-non-absorptive portion 167. The blood-absorptive portion can include the lysine as powder or in a reservoir.

FIG. 1H shows a device 170 with a body 172 having one or more chamber layers 174 having the hemostatic composition 132. The chamber layers 174 can be separated by body layers 176, the body layers 176 forming the chamber layers 174. Also, the hemostatic composition can be in the body 172 or between the layers or in the layers 174.

FIG. 1I shows a device 180 having a body 182 having a detachable tab 184 defining at least one side of a chamber 186 having the hemostatic composition 132. The detachable tab 184 can be torn off of the body 182, partially or entirely so as to make a conduit into the chamber 186. The detachable tab 184 can be separated from the body 184 with a perforation that allows for tearing the detachable tab 184 from the body 182. The detachable tab 184 may also be dissolved off of the body 182 by blood. Also, the detachable tab 184 may cover the chamber 186 when dry, but become permeable to the lysine upon soaking blood. The body 182 can be any shape.

Figure 1J:
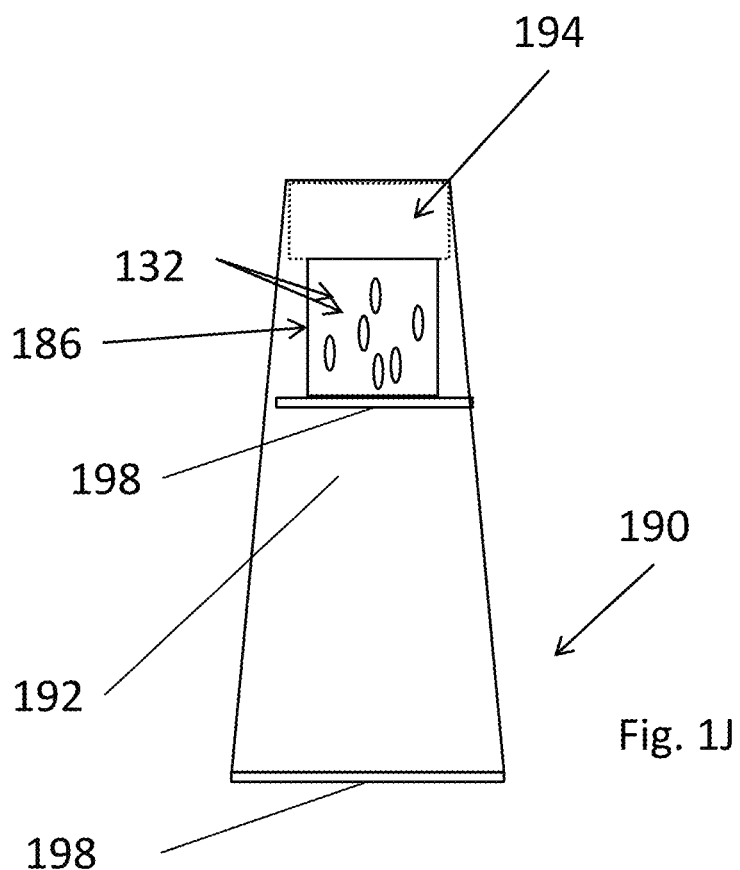

FIG. 1J shows a device 190 having a body 192 with a blood-dissolvable portion 194 defining at least one side of a chamber 186 having the hemostatic composition 132.

Figure 1K:
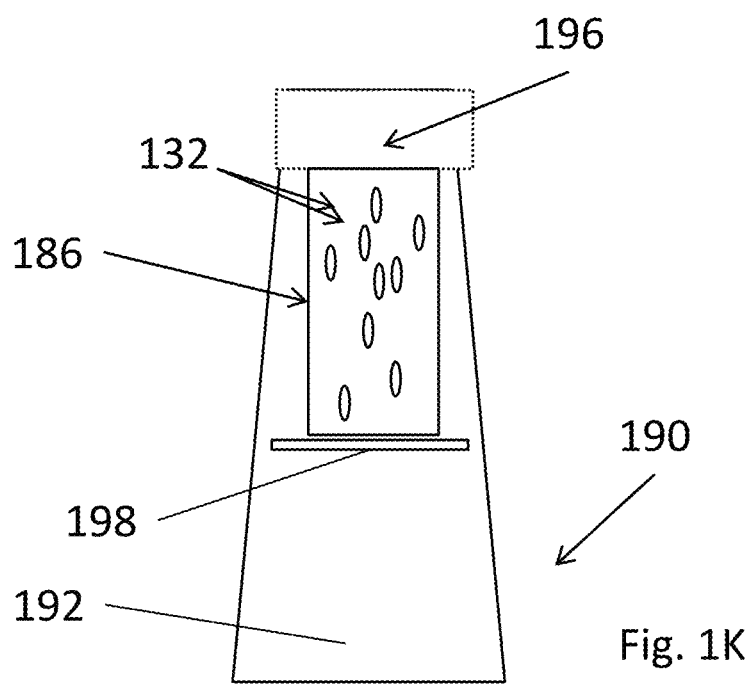

FIG. 1K shows a device 190 with a body 192 having a blood-permeable member 196 defining at least one side of a chamber 186 having the hemostatic composition 132.

In one embodiment, the devices 190 of FIGS. 1J and 1K show the body 192 having a blood-impermeable member 198 defining at least one side of a chamber 186 having the hemostatic composition 132. The devices 190 can include the body 192 having a blood-impermeable member 198 defining at least one side of a chamber 186 having the hemostatic composition 132, the blood-impermeable member 198 being located at a bottom portion of the body, the bottom portion being opposite of a top portion with respect to the chamber 186, the top portion being configured to be inserted into a nasal passageway and allowing for blood to penetrate into the chamber 186. The body 192 can have a blood-impermeable member 198 defining at least one side of a chamber 186 having the hemostatic composition 132, the blood-impermeable member 198 being opposite of a top side with respect to the hemostatic composition 132. The body 192 can have a blood-impermeable member 198 defining at least one side surface of the body 192. The body 192 can have a blood-impermeable member 198 defining at least one side of a chamber 186 having the hemostatic composition 132 and a blood-permeable member 194 defining at least one side of the chamber 186. The body 192 can have a blood-impermeable member 198 defining at least one side of a chamber 186 having the hemostatic composition 132 and a blood-permeable member 194 defining at least one side of the chamber 186 opposite of the blood-impermeable member 198. The body 192 having a blood-impermeable member 198 defining at least one side of a chamber 186 having the hemostatic composition 132 and a blood-permeable member 194 defining at least one side of the chamber 186. While not shown, the blood-impermeable member 198 may encompass the chamber 186 except for the top side of the chamber 186. As such, the blood-impermeable member 198 may cooperate with member 194 or 196 to define the chamber 186.

Figure 2A:
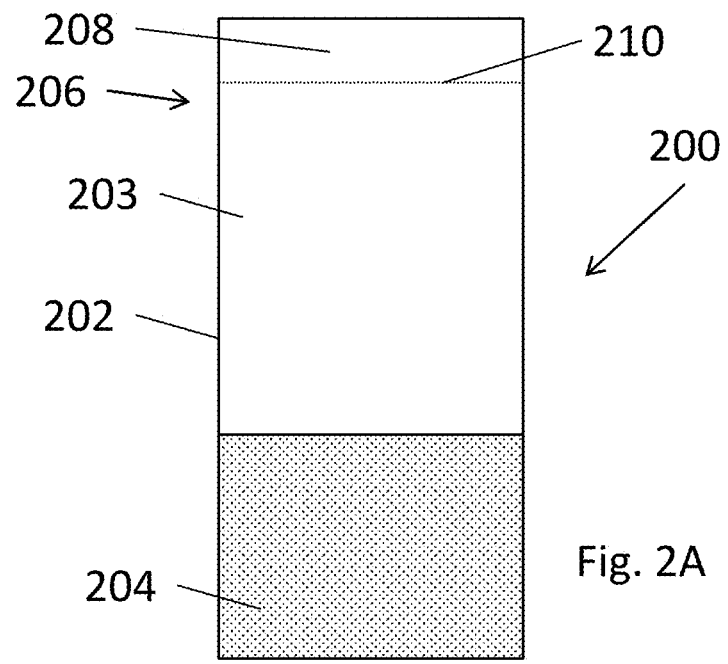
FIGS. 2A-2B illustrate embodiments of packages having hemostatic compositions.

FIG. 2A illustrates an embodiment of a medical device 200 that includes a package body 202 forming a chamber 203 having the hemostatic composition 204 therein. The hemostatic composition 204 can include the lysine hemostatic composition described herein. The package body 202 can include a first end 206 adapted to be inserted proximal or into a nasal passageway. The first end 206 includes a sealed end 208 that can be opened easier than the other edges or seals. The sealed end 208 can include a portion with a lighter adhesive or other configuration that allows the sealed end to be opened, such as by tearing, peeling, or the like. Also, the sealed end 208 can be sealed in a manner that the sealed end 208 opens upon applying pressure to the package body 202. As such, the chamber 203 can have gas, such as air, which may or may not be pressurized compared to surrounding atmospheric pressure. For example, applying pressure or force can open the sealed end 208, which can burst the package body 202 at the sealed end 208. The package body 202 can be a blister package that is openable. The package body 202 can include a tear line 210, which is configured to tear easily with hands. Tear lines 210 are well known, and may be configured as a weakness, perforation, partial or initial tear, tear partition, openable seal or other configuration that allows tearing the first end 206 open to open the chamber 203 so that the hemostatic composition 204 can be released. When not opened, the chamber 203 can be airtight.

The body can be in various configurations. In some instances, the body described herein can be a unitary body. In other instances, the body described herein can be made from multiple members coupled together.

In one embodiment, the body associated with the hemostatic composition can be place in an airtight chamber of a package. For example, the package body 202 of FIG. 2B can include an absorbent body 214 having the hemostatic hemostatic composition 204. The package body 202 can be opened at the sealed end 208, and the absorbent body 214 can be removed therefrom in order to deliver the hemostatic hemostatic composition. The absorbent body 214 may be applied to blood or introduced into a bleeding passageway, such as a bleeding nostril.

Figure 2B:
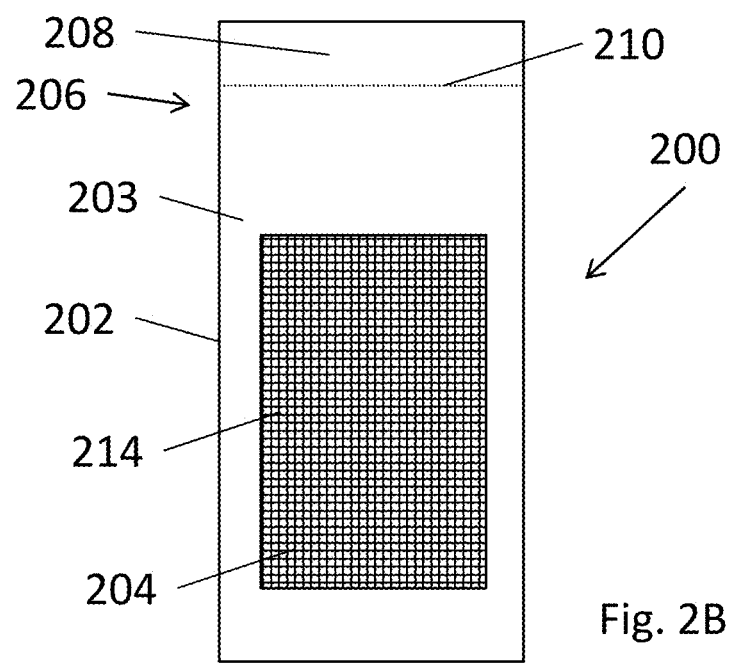

FIG. 2B shows a device comprising an absorbent member located in a burst chamber, wherein the absorbent member can be extracted from the burst chamber upon bursting and inserted in a nasal passageway, optionally, the bursting can spray the hemostatic composition into the nose, and then the absorbent member having the hemostatic composition can be withdrawn from the burst chamber and inserted into the nasal passageway.

Figure 2C:
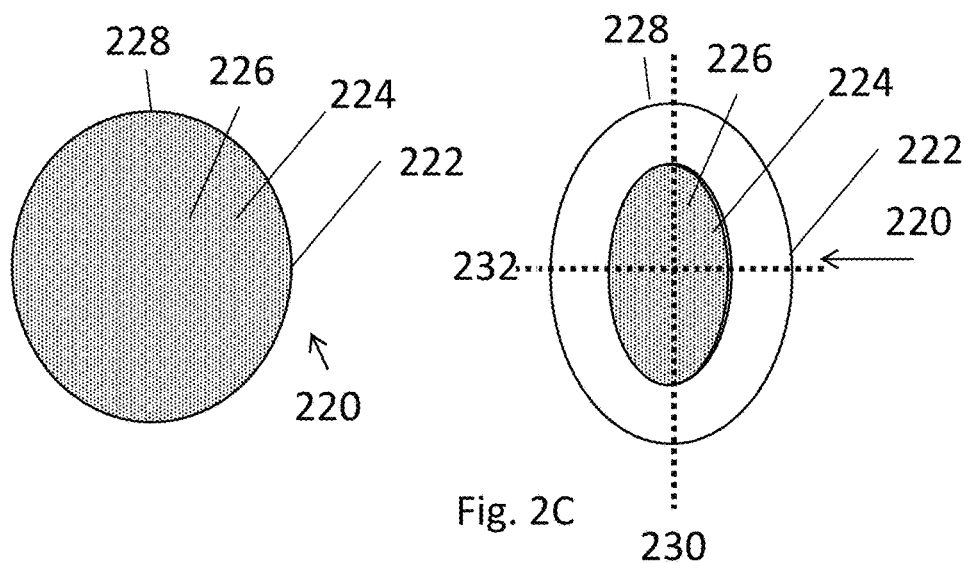
FIGS. 2C-2G illustrate embodiments of containers containing sprayable dry hemostatic compositions.

FIG. 2C illustrates an embodiment of a device 220 with a body 222 that includes a burst chamber 224 that contains the hemostatic composition 226. The burst chamber 224 can be characterized by the body shell 228 defining an inner chamber 224 having the hemostatic composition 226, where the body shell 228 is configured to burst upon receiving a predetermined force or pressure, and such burst releases the hemostatic composition 226. The bursting of the burst chamber 224 can spray the hemostatic composition as a liquid, gel, or powder or any other sprayable hemostatic composition. Often, the burst chamber includes the hemostatic composition and pressurized gas. The pressurized gas can facilitate spraying the hemostatic composition upon bursting. However, the burst chamber 224 is not required to be pressurized, where the bursting of the burst chamber 224 causes the hemostatic composition to be ejected. While the body 222 is illustrated to be spherical, the body could be configured to have a polygon cross-section. The body shell 228 diameter or distance from one side to the other (e.g., cross-sectional dimension) can range depending on the application. For example, a single macro-scale burst chamber 224 can be used to administer the entire dose of a hemostatic composition. The macro-scale burst chamber for a nasal application can range in cross-sectional dimension from about 5 mm to about 5 cm, or from about 1 cm to about 4 cm, or from about 2 cm to about 3 cm. or about 2.5 cm.

A micro-scale burst chamber can be included in a matrix or body of a macro-scale device. For example, an absorbent member can contain a plurality of micro-scale burst chambers in a chamber and/or embedded a matrix of the body and/or located on the surface of the body or anywhere else. A micro-scale burst chamber can be configured to burst upon receiving a predefined pressure or force, such as that which is applied by fingers during squeezing, which can be squeezing a single micro-scale burst chamber or a plurality of micro-scale burst chambers. The micro-scale burst chamber can be a core/shell micro-sphere that has a burstable shell having the hemostatic composition core. Examples of size range of micro-scale burst chambers can be from about 1 μm to 1000 μm, from about 50 μm to 750 μm, or 100 μm to 500 μm, or 250 μm to 300 μm. A plurality of micro-scale chambers can be used for a single administration of the hemostatic composition.

In one embodiment, the device can include a burst chamber that contains the hemostatic composition, the burst chamber being elongate in a longitudinal axis 230 and configured to burst open at one end of a longitudinal axis 230 upon receiving force or pressure from a lateral axis 232 (see FIG. 2C).

Figure 2D:
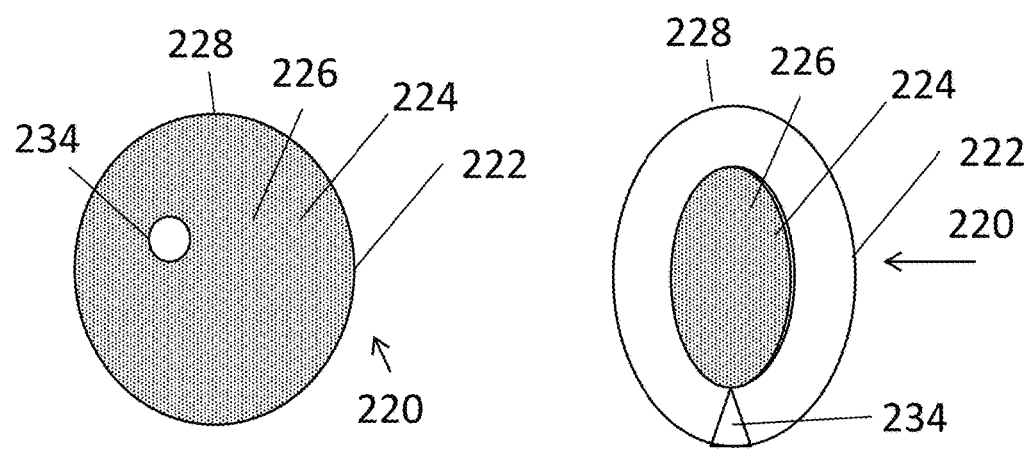

The device 220 can include a body 222 comprising a burst chamber 224 that contains the hemostatic composition 226, the burst chamber 224 being configured to bust through an opening 234 in the body 222 upon the burst chamber 224 being compressed as shown in FIG. 2D.

Figure 2E:
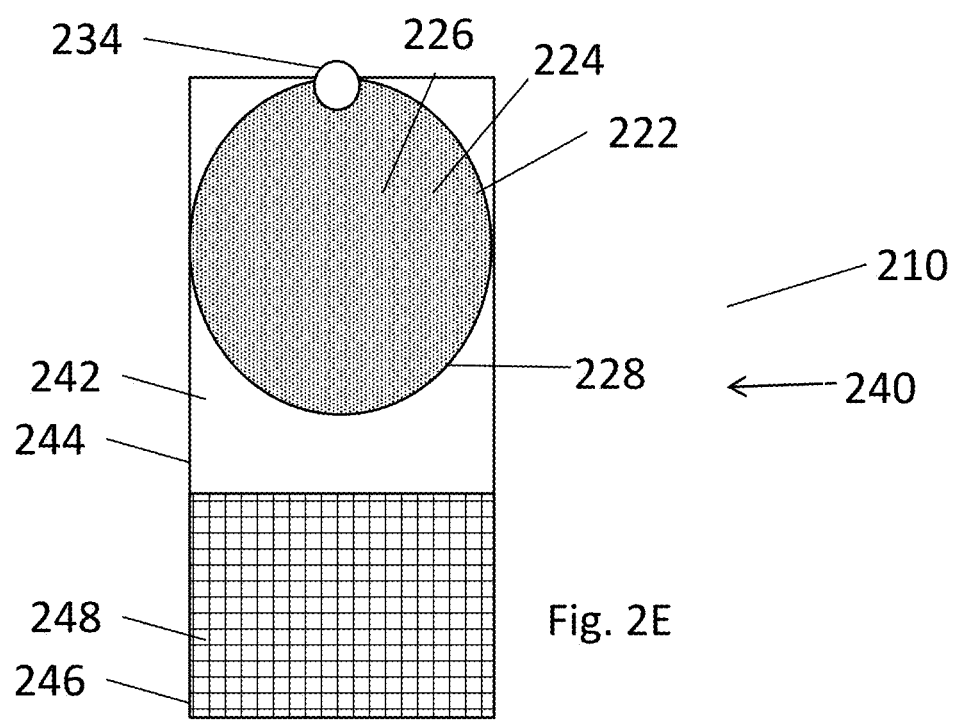

FIG. 2E shows a device 240 having a body 242 comprising a burst chamber 224 located in an end of an absorbent member 244, the burst chamber 224 containing the hemostatic composition 226 and the device 240 being configured to spray the hemostatic composition upon bursting the burst chamber 224. For example, the burst chamber 224 can include an opening 234 or have one created upon receiving lateral force or pressure. The end 246 opposite of the opening 234 can be resistant to permeation of the lysine, and may optionally include a permeation-resistant member 248, which can be blood-resistant. A hydrophobic polymer sheet, memory foam, or plastic member can be used. Accordingly, the burst chamber 224 being configured to burst open at one end upon being exposed to blood. The burst chamber 224 can be configured to burst open at one end of a longitudinal axis upon receiving force or pressure from a lateral axis. The hemostatic composition is released from an end or opening 234 upon the burst chamber 224 bursting. A spray mechanism can be associated with a chamber having the hemostatic composition, the spray mechanism being capable of spraying the hemostatic composition from the chamber, wherein the spray chamber is a burst chamber with or without the hemostatic composition and the chamber sprays the hemostatic composition by bursting the burst chamber.

Figure 2F:
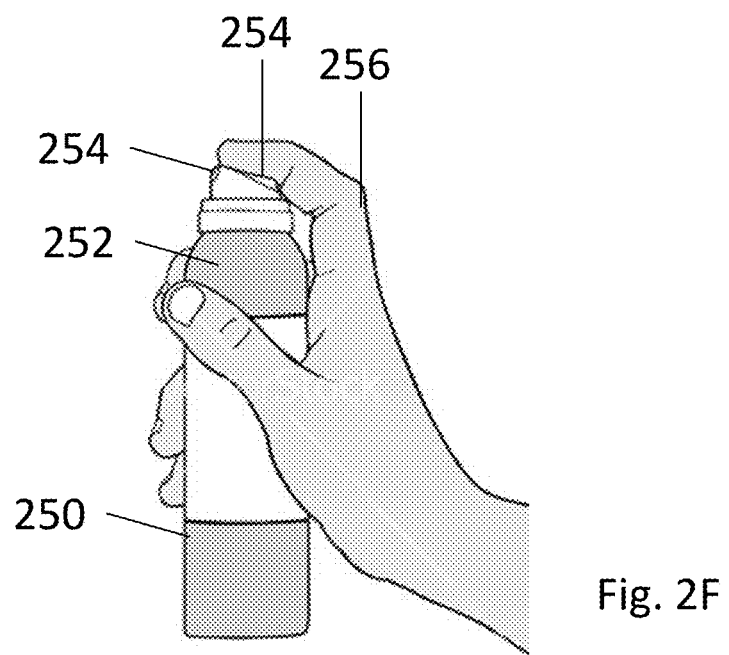

In one embodiment, FIG. 2F illustrates a body 250 that can be configured as a pressurized chamber 252 that contains the hemostatic composition. The pressurized chamber 252 can be configured to release the hemostatic composition through an opening 254 upon being depressurized. The opening 254 can be a nozzle, such as a common depressurization spraying nozzle. The body can include a pressurized chamber that contains the hemostatic composition, the pressurized chamber being configured to release the hemostatic composition through an opening upon being depressurized by a depressurization device. The device can include a trigger mechanism 256 operably coupled to the pressurized chamber 252 such that actuation of the trigger mechanism 256 (e.g., by a finger 257) releases the hemostatic composition through an opening 254. The device can include a spray mechanism associated with a chamber having the hemostatic composition, the spray mechanism being capable of spraying the hemostatic composition from the chamber.

Figure 2G:
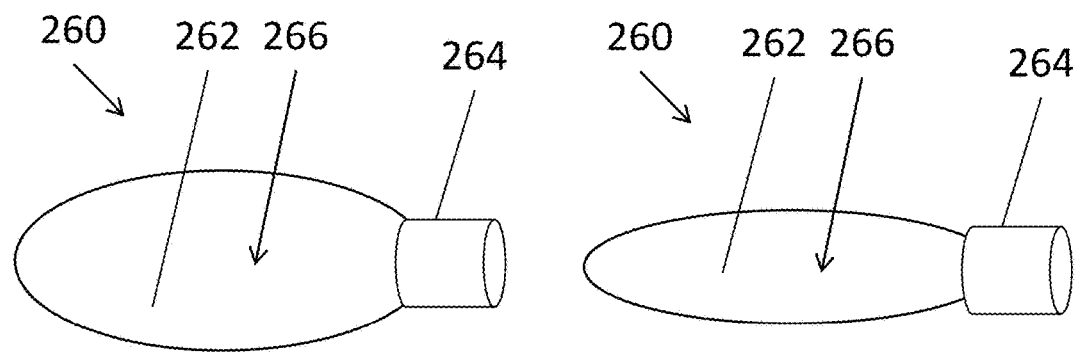

FIG. 2G illustrates a device 260 with a pump 262 (e.g., any pump, shown as bulb pump) operably coupled to a chamber 264 having the hemostatic composition, the pump 262 being adapted to spray the hemostatic composition from the chamber 264 upon being operated. As shown, squeezing the pump can cause pressure to force the hemostatic composition from the chamber 264 for delivery. The chamber 264 can be adapted to be received into a nostril so that the hemostatic composition can be delivered to inhibit or stop a nose bleed. The pump 262 can be operably coupled to the chamber 264 having the hemostatic composition, the pump 262 being adapted to spray the hemostatic composition as a powder. The pump 262 can be operably coupled to a chamber 264 having the hemostatic composition, the pump 262 being adapted to spray the hemostatic composition as powdered dry particles. As shown, the pump 262 includes a bulb that has an internal chamber 266 with the hemostatic composition and that sprays the dry hemostatic composition particles upon being squeezed (e.g., with or without the chamber 264 having the hemostatic composition, and the chamber 264 can be omitted). The end of the bulb can be adapted to fit into a nostril.

Figure 2H:
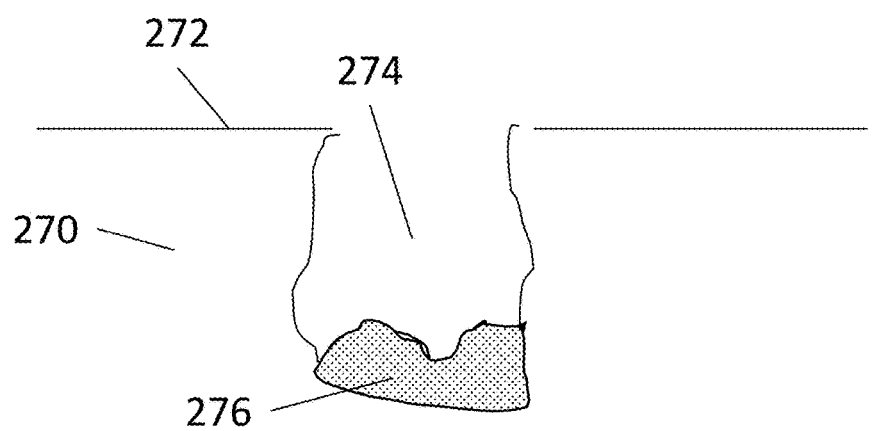
FIG. 2H illustrates an embodiment of a body having recesses containing a hemostatic composition.

In one embodiment, any of the devices described herein can include a body having the hemostatic composition sprinkled on an outer surface, the hemostatic composition being powdered and capable of being removed. The body 270 can include a surface 272 having receptacles 274 for the powdered hemostatic composition 276 on an outer surface or inner, such that the powder can be rubbed or sprinkled off, which can be seen in FIG. 2H.

In one embodiment, the hemostatic composition included in the device for delivery is a different hemostatic composition that may or may not have lysine or lysine derivative, optionally the different hemostatic composition includes an active agent. The different hemostatic composition can include any drug agent for delivery, such as for delivery to a nose to stop nose bleeding or for any other reason to deliver the drug agent.

In one embodiment, the hemostatic composition may not be included in the device. Instead, the device may alternately include an active agent composition, where the active agent composition is devoid of a hemostatic agent. As such, the devices described herein can deliver other agents other than hemostatic agents. That is, the devices can be used as general drug delivery devices.

In one embodiment, the device can be configured or shaped or otherwise adapted for delivery to certain places in a patient. For example, the device can be configured to deliver the composition to a nasal passageway; to spray the composition into a nasal passageway; to aerosol the composition into a nasal passageway; to apply the composition into a membrane of a nasal passageway; to contact the composition into a membrane of a nasal passageway; to spray the composition into blood in a bleeding nasal passageway; to contact the hemostatic composition to blood in a bleeding nasal passageway; to absorb blood until the blood contacts the hemostatic composition, the blood being from into a bleeding nasal passageway. The body can be configured as a nose plug. The body can be configured a nose plug configured to block blood flow. The body being biodegradable, or the body can be biostable. The body can be blood-stable so as to retain its integrity when exposed to blood. The body can be blood-degradable so as degrade and expose the hemostatic composition to the blood upon contact with the blood.

The body can be made of various materials. In one example, the body includes hydroxyethylcellulose and/or amylopectin.

In one embodiment, a device can be configured for coagulating blood in a nasal passageway, where the device is configured for insertion into the nose. A device for coagulating blood in a nasal passageway can be configured to spray the hemostatic composition into the nasal passageway. A device for coagulating blood in a nasal passageway can be configured to apply the hemostatic composition to blood in the nasal passageway. A device for coagulating blood in a nasal passageway can be configured to apply the hemostatic composition to a surface of the nasal passageway. A device for coagulating blood in a nasal passageway can be configured to apply the hemostatic composition to a membrane of the nasal passageway. A device for coagulating blood can be configured to apply the hemostatic composition to blood. A device for coagulating blood can be configured to apply the hemostatic composition to a wound. A device for coagulating blood can be configured to apply the hemostatic composition to a vagina during menstruation. A device for coagulating blood can be configured to apply the hemostatic composition to an external wound in skin. A device for coagulating blood can be configured to apply the hemostatic composition to an internal would, the device being blood-stable so as to be capable of being withdrawn from the internal wound intact. A device for coagulating blood can be configured to be inserted into a wound so as to apply the hemostatic composition to blood in the wound.

The body can be a blister pack having the hemostatic composition therein. The hemostatic composition can be a powder that can be obtained from the blister pack. The hemostatic composition can be on an absorbent member or other device, which can be stored in the blister pack prior to use.

Figure 2I:
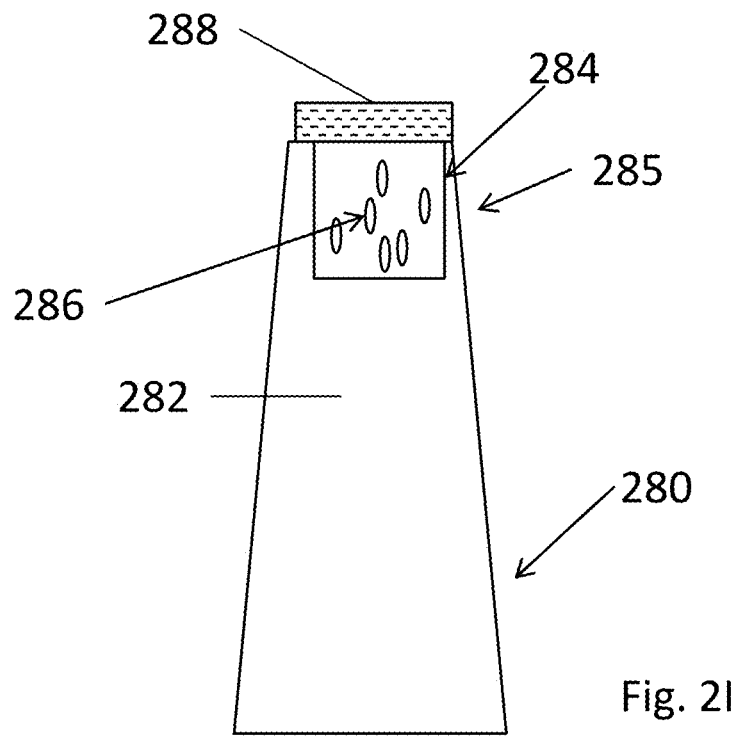
FIGS. 2I-2K illustrate embodiments of devices having hemostatic compositions.

The device 280 of any of the embodiments, such as shown in FIG. 2I, can include a body 282 having a recess 284 at a first end 285, the recess 284 having the hemostatic composition 286, the first end 285 being adapted to be inserted into a nasal passageway.

Figure 2J:
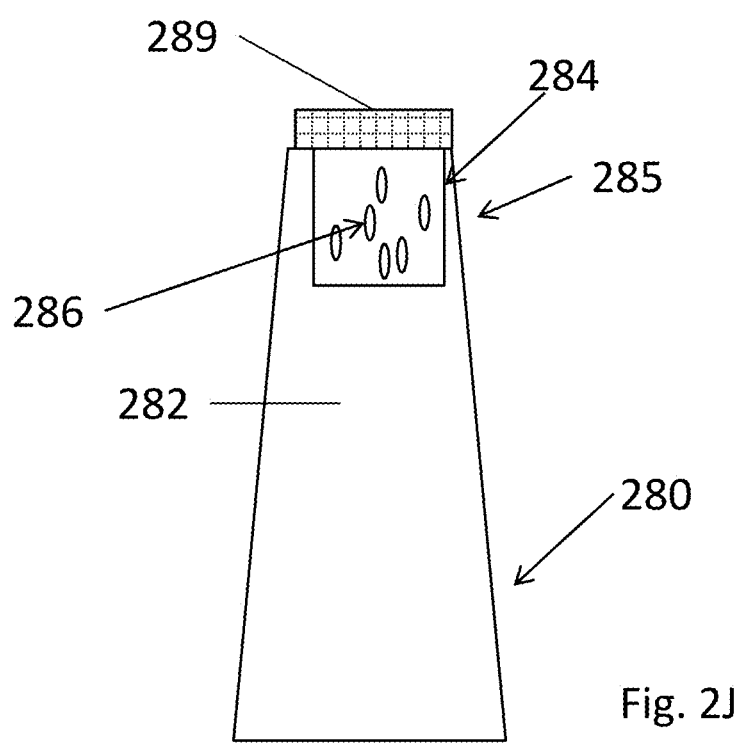

The device of any of the embodiments, such as in FIG. 2I can include a body 282 having a recess 284 at a first end, the recess 284 having the hemostatic composition 286, a removable cover 288 (e.g., tear-off cover) over the recess in the first end, the first end being adapted to be inserted into a nasal passageway. FIG. 2J shows the body 282 having the recess 284 at a first end 285, the recess 284 having the hemostatic composition 286, a blood-degradable cover 289 over the recess 284 in the first end 285, the first end 285 being adapted to be inserted into a nasal passageway. The cover can also be blood-permeable. Also, the cover can be an openable cover.

Figure 2K:
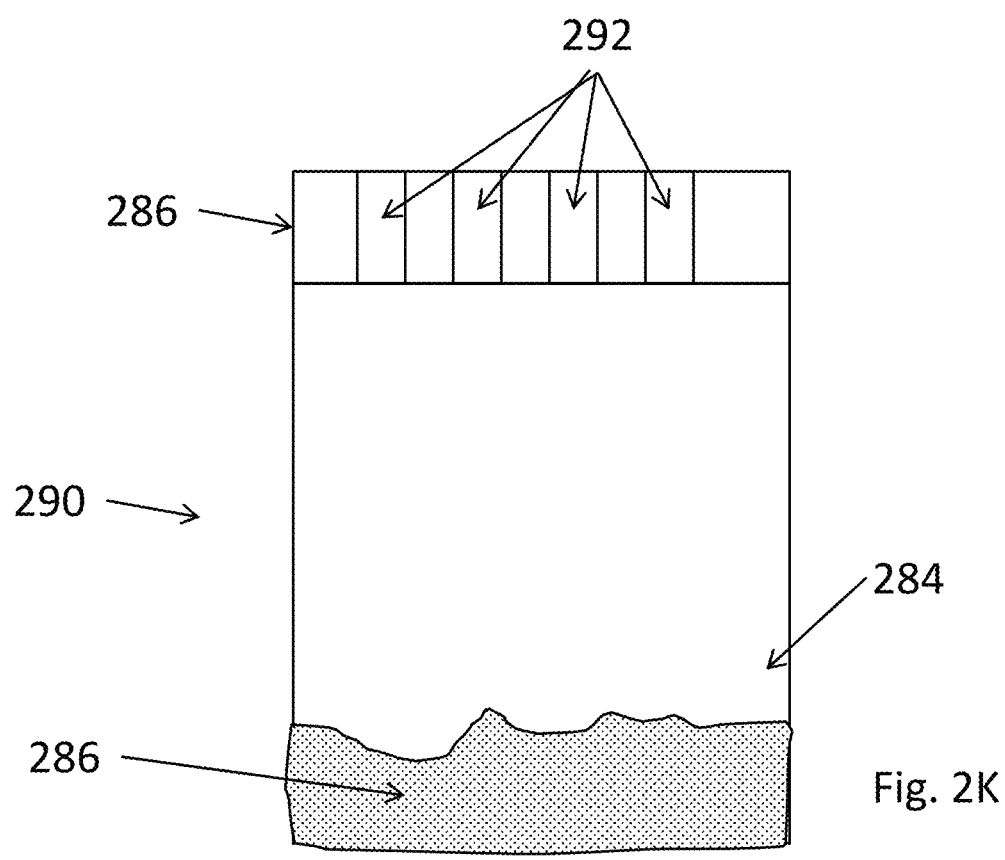

A hemostatic composition flow-rate controlling member can be over the recess. FIG. 2K shows a recess 284 with the hemostatic composition 286 having a hemostatic composition flow-rate controlling member 290. Such a member 290 can be similar to a cover for the recess 284 that has perforations, holes, apertures, pores, conduits or the like 292 that extend from one side to another, so as to fluidly couple the internal part of the recess 284 and the outside of the device. The hemostatic composition 286 can be sprayed or otherwise emitted or released through the holes 292 to administer the hemostatic composition 286.

In one embodiment, the present invention includes a method for coagulating blood, the method includes: providing the hemostatic composition or device of one of the embodiments; and applying the hemostatic composition to blood so as to cause the blood to coagulate. The method can include one or more of the following: spraying the hemostatic composition onto blood; spraying the hemostatic composition into blood; spraying the hemostatic composition onto a nasal passageway; spraying the hemostatic composition onto a wound; spraying the hemostatic composition onto a surgical site; contacting the hemostatic composition onto blood; inserting the hemostatic composition into blood; inserting the hemostatic composition onto a nasal passageway; inserting the hemostatic composition onto a wound; inserting the hemostatic composition onto a surgical site; applying the hemostatic composition as a powder; applying the hemostatic composition as a gel; applying the hemostatic composition as a paste.

In one embodiment, the hemostatic composition is devoid of a liquid. In another embodiment, the hemostatic composition includes a liquid. The hemostatic composition can be in a liquid format. The hemostatic composition can be in a fluidic format that is non-liquid. The hemostatic composition can be a solid, such as a powdery solid.

The method can include administering the hemostatic composition so as to cause the blood to clot or otherwise coagulate. The coagulation can occur in a nasal passageway, wound, surgical site, or vagina.

In one embodiment, the method can include coagulating the blood away from a blood vessel. The coagulation can occur in a nasal passageway. The coagulation can occur on a nasal membrane. The hemostatic composition can be applied to blood for coagulating blood within a nasal passageway so as to inhibit the blood from flowing in the nasal passageway or out from the nasal passageway. The lysine hemostatic composition can inhibit blood from flowing from a nasal passageway.

In one embodiment, the method can include coagulating the blood at or in a blood vessel. This can include coagulation at a ruptured blood vessel so as to induce healing of the ruptured blood vessel.

The method for applying the hemostatic composition can include releasing the hemostatic composition from the device. This can include one or more of: spraying the hemostatic composition from the device; aerosolizing the hemostatic composition from the device; squeezing the device so as to release the hemostatic composition therefrom; activating a mechanism in the device so as to release the hemostatic composition therefrom; smearing, rubbing, or otherwise contacting the hemostatic composition to blood or a mucus membrane having blood thereon; or applying the device of one of the embodiments to the blood so that the hemostatic composition causes the blood to coagulate.

In one embodiment, the hemostatic composition can be provided to the device so that the device can apply the hemostatic composition as described herein. For example, the powder can be dumped into a reservoir, then ejected from the reservoir into a nasal passageway onto blood or a nasal membrane.

The method can include applying the lysine or lysine derivative to blood in an effective amount to inhibit plasminogen. The method can include applying the lysine or lysine derivative in an effective amount to inhibit plasminogen conversion to plasmin in the blood. The method can include applying the lysine or lysine derivative in an effective amount to inhibit formation of plasmin. The method can include applying the lysine or lysine derivative in an effective amount to inhibit fibrinolysis. The method can include applying the lysine or lysine derivative in an effective amount to occupy a lysine binding site on plasminogen so inhibit conversion to plasmin. The method can include applying the lysine or lysine derivative in an effective amount to occupy a lysine binding site in a Kringle domain on plasminogen so inhibit conversion to plasmin. The method can include applying the lysine or lysine derivative in an effective amount to cause blood coagulation on a nasal membrane. The method can include applying the lysine or lysine derivative so as to be located in a nasal passageway. The method can include applying the lysine or lysine derivative so as to be located on a mucosal membrane in the nasal passageway. The method can include applying the lysine or lysine derivative in an aerosoled powder format. The method can include applying the lysine or lysine derivative as a plurality of lysine molecules in a powder reservoir. The method can include applying the lysine or lysine derivative to blood from a medical device. The method can include applying the lysine or lysine derivative to blood from an absorbent member. The method can include applying the lysine or lysine derivative to blood from in a cylindrical member at a first end, the first end being configured for insertion into a nasal passageway or vagina. The method can include releasing a memory member from a first compressed shape and a second expanded shape in a nasal passageway, wound, surgical site, or vagina, the memory member being in a device having the hemostatic composition. The method can include other steps for application of the hemostatic composition.

The present invention can include a method of manufacturing a blood coagulating device. Such a manufacturing method can include one or more of: forming a body; and associating a hemostatic composition with the body, the hemostatic composition being of one of the embodiments, the body being of one of the embodiments, such as one of the devices. The method can include one or more of the following: forming the body to include a medical device; forming the body to include an absorbent member; forming the body to include a cylindrical member having a first end having the hemostatic composition, the first end being configured for insertion into a nasal passageway; forming the an absorbent member; forming the body to include a memory member associated with the body, the memory member having a first compressed shape and a second expanded shape; forming the body to include gauze; forming the body to include a carrier substrate; forming the body to comprise a hemostatic carrier substrate; forming the body to comprise a mesh hemostatic carrier substrate; forming the body to comprise a foam hemostatic carrier substrate; forming the body to comprise a polymeric hemostatic carrier substrate; forming the body to comprise a cellulosic hemostatic carrier substrate; forming the body to comprise a tissue paper substrate having the lysine or lysine derivative; forming the body to comprise a polysaccharide; forming the body to have a chamber having the hemostatic composition; forming the body to have a surface having the hemostatic composition; forming the body to comprise the hemostatic composition embedded therein; forming the body to comprise the hemostatic composition thereon; forming the body to comprise interstitial spaces having the hemostatic composition; forming the body to have one or more depots of the hemostatic composition; forming the body to have one or more chamber layers having the hemostatic composition; forming the body to be cylindrical; forming the body to be tapered from one end to an opposite end; forming the body to have a shaped adapted to be received into a nasal passageway; forming the body to have a core and a shell; forming the body to have a memory member core with an absorptive shell; forming the body to have a detachable tab defining at least one side of a chamber having the hemostatic composition; forming the body to have a blood-dissolvable portion defining at least one side of a chamber having the hemostatic composition; forming the body to have a blood-permeable member defining at least one side of a chamber having the hemostatic composition; forming the body to have a blood-impermeable member defining at least one side of a chamber having the hemostatic composition; forming the body to have a blood-impermeable member defining at least one side of a chamber having the hemostatic composition, the blood-impermeable member being located at a bottom portion of the body, the bottom portion being opposite of a top portion with respect to the chamber, the top portion being configured to be inserted into a nasal passageway; forming the body to have a blood-impermeable member defining at least one side of a chamber having the hemostatic composition, the blood-impermeable member being opposite of a top side with respect to the hemostatic composition; forming the body to have a blood-impermeable member defining at least one side surface of the body forming the body to have a blood-impermeable member defining at least one side of a chamber having the hemostatic composition and a blood-permeable member defining at least one side of the chamber; forming the body to have a blood-impermeable member defining at least one side of a chamber having the hemostatic composition and a blood-permeable member defining at least one side of the chamber opposite of the blood-impermeable member; forming the body to have a blood-impermeable member defining at least one side of a chamber having the hemostatic composition and a blood-permeable member defining at least one side of the chamber; forming the body to be a blister package; forming the body to have a tear partition; forming the body to have an openable seal; forming the body to have an airtight chamber having the hemostatic composition therein; forming the body to be a unitary member; forming the body to comprise multiple members; locating the body in an airtight chamber of a package; forming the body to have a blood-absorptive portion and a blood-non-absorptive portion, the hemostatic composition being associated with the blood-absorptive portion; forming the body to have a blood-absorptive portion that includes a memory member and a blood-non-absorptive portion, the hemostatic composition being associated with the blood-absorptive portion; forming the body to have a blood-absorptive portion and a blood-non-absorptive portion, the hemostatic composition being associated with the blood-absorptive portion and the blood-non-absorptive portion; comprising forming the body to have a blood-absorptive portion and a blood-non-absorptive portion, the hemostatic composition being between the blood-absorptive portion and blood-non-absorptive portion; forming the body to comprise a burst chamber that contains the hemostatic composition; forming the body to comprise a burst chamber that contains the hemostatic composition, the burst chamber being configured to burst open at one end of a longitudinal axis upon receiving force or pressure from a lateral axis; forming the body to comprise a burst chamber that contains the composition, the burst chamber being configured to bust through an opening upon the burst chamber being compressed; forming the body to comprise a burst chamber located in an end of an absorbent member, the burst chamber containing the hemostatic composition and being configured to spray the hemostatic composition upon bursting the burst chamber; forming the body to comprise a burst chamber that contains the hemostatic composition, the burst chamber being configured to burst open at one end upon being exposed to blood; forming the body to comprise a burst chamber that contains the hemostatic composition, the burst chamber being configured to burst open at one end of a longitudinal axis upon receiving force or pressure from a lateral axis; forming the device with a burst chamber such that the hemostatic composition is released from an end or opening upon the burst chamber bursting; forming the body to comprise a pressurized chamber that contains the hemostatic composition, the pressurized chamber being configured to release the hemostatic composition through an opening upon being depressurized; configuring the body to comprise a pressurized chamber that contains the hemostatic composition, the pressurized chamber being configured to release the hemostatic composition through an opening upon being depressurized by a depressurization device; coupling a trigger mechanism to the pressurized chamber such that actuation of the trigger mechanism releases the hemostatic composition through an opening; coupling a pump to a chamber having the hemostatic composition, the pump being adapted to spray the hemostatic composition upon being operated; coupling a pump to a chamber having the hemostatic composition, the pump being adapted to spray the hemostatic composition as a powder; coupling a pump to a chamber having the hemostatic composition, the pump being adapted to spray the hemostatic composition as powdered dry particles, optionally, the pump includes a bulb (e.g., turkey baster bulb) that has an internal chamber with the hemostatic composition and that sprays the dry hemostatic composition particles upon being squeezed; forming an absorbent member and located the absorbent member in a burst chamber, wherein the absorbent member can be extracted from the burst chamber upon bursting and inserted in a nasal passageway, optionally, the bursting can spray the hemostatic composition into the nose, and then the absorbent member having the hemostatic composition can be withdrawn from the burst chamber and inserted into the nasal passageway; forming the body to have the hemostatic composition sprinkled on an outer surface, the hemostatic composition being powdered and capable of being removed; forming the body to have receptacles in an outer surface and locating the powdered hemostatic composition in the receptacles in the outer surface, such that the powder can be rubbed or sprinkled off the body; coupling a spray mechanism with a chamber having the hemostatic composition, the spray mechanism being capable of spraying the hemostatic composition from the chamber; coupling a spray mechanism with a chamber having the hemostatic composition, the spray mechanism being capable of spraying the hemostatic composition from the chamber, wherein the spray chamber is a burst chamber with or without the hemostatic composition and the chamber sprays the hemostatic composition by bursting the burst chamber; or configuring the device so as to deliver the hemostatic composition to a nasal passageway.

The device can have various configurations for delivery of the hemostatic composition, and such configurations have different manufacturing requirement. Accordingly, the manufacturing results in one or more of the following: the device is configured to spray the hemostatic composition into a nasal passageway; configured to aerosol the hemostatic composition into a nasal passageway; configured to apply the hemostatic composition into a membrane of a nasal passageway; configured to contact the hemostatic composition to a membrane of a nasal passageway; configured to spray the hemostatic composition into blood in a bleeding nasal passageway; configured to contact the hemostatic composition to blood in a bleeding nasal passageway; configured to absorb blood until the blood contacts the hemostatic composition, the blood being from into a bleeding nasal passageway; configured as a nose plug; or the body is configured a nose plug configured to block blood flow.

The manufacture method can include one or more of: forming the body to be biodegradable; forming the body to be biostable; forming the body to be blood-stable so as to retain its integrity when exposed to blood; forming the body to be blood-degradable so as degrade and expose the hemostatic composition to the blood upon contact with the blood; forming the body to include hydroxyethylcellulose and/or amylopectin; forming the device for insertion into the nose; forming the device to spray the hemostatic composition into the nasal passageway; forming the device to apply the hemostatic composition to blood in the nasal passageway; forming the device to apply the hemostatic composition to a surface of the nasal passageway; forming the device to apply the hemostatic composition to a membrane of the nasal passageway; forming the device to apply the hemostatic composition to blood; forming the device to apply the hemostatic composition to a wound; forming the device to apply the hemostatic composition to a vagina before or during menstruation; forming the device to apply the hemostatic composition to an external wound in skin; forming the device to apply the hemostatic composition to an internal wound, the device being blood-stable so as to be capable of being withdrawn from the internal wound intact; forming the device to be inserted into a wound so as to apply the hemostatic composition to blood in the wound; forming the body to be a blister pack having the hemostatic composition therein; forming the body to be in a contracted form and having an expanded form upon contact with liquid, such as blood; forming the body to be blood-expandable from a first smaller size to a second larger size upon exposure to blood; forming the body to have a recess at a first end, the recess having the hemostatic composition, the first end being adapted to be inserted into a nasal passageway; forming the body to have a recess at a first end, the recess having the hemostatic composition, applying a removable cover over the recess in the first end, the first end being adapted to be inserted into a nasal passageway; forming the body to have a recess at a first end, the recess having the hemostatic composition, applying a blood-degradable cover over the recess in the first end, the first end being adapted to be inserted into a nasal passageway; forming the body to have a recess at a first end, the recess having the hemostatic composition, applying a blood-permeable cover over the recess in the first end, the first end being adapted to be inserted into a nasal passageway; forming the body to have a recess at a first end, the recess having the hemostatic composition, forming a tear-off cover over the recess in the first end, the first end being adapted to be inserted into a nasal passageway; or forming the body to have a recess at a first end, the recess having the hemostatic composition, forming an openable cover over the recess in the first end, the openable cover being configured to be opened to expose the hemostatic composition, the first end being adapted to be inserted into a nasal passageway.

The method of manufacturing a device to deliver the hemostatic composition can include: obtaining a substrate; applying the hemostatic composition to a first surface of the substrate; folding the substrate so that a first portion of the first surface of substrate contacts a second portion of the first surface of the substrate; and fastening the first portion to the second portion. The method can include adhering the first portion to the second portion. The method can include comprising rolling the folded substrate into a cylindrical form. The method can include applying the hemostatic composition into a crease in the substrate and folding the substrate at the crease so that the hemostatic composition is at an end or edge of the device. In one aspect, the fastening of one portion to anther portion is adhering. The method can include applying an adhesive to a second surface of the substrate such that rolling the substrate forms a cylindrical member; the device can be prepared so that the hemostatic composition is located in a plurality of layers of the rolled substrate; or a tear portion that when torn opens the device to expose the hemostatic composition.

In one embodiment, a manufacturing method can include repairing a hemostatic composition that is a different hemostatic composition that may or may not have lysine or lysine derivative, optionally the hemostatic composition includes an active agent, and combining the different hemostatic composition with the body, where the hemostatic composition having lysine may or may not be combined with the body (e.g., that is, the device can include any other nutraceutical and/or pharmaceutical composition that may or may not have lysine or lysine derivative). Thus, the devices of the invention described herein can be used with other compositions, such as non-lysine composition. The composition may or may not be hemostatic. The compositions can administer a pharmaceutical or a nutraceutical or other. The methods can use compositions in the devices that are not hemostatic, but do include other active agents, and thereby the devices can be used to deliver other active agents other than hemostatic agents.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 15A:
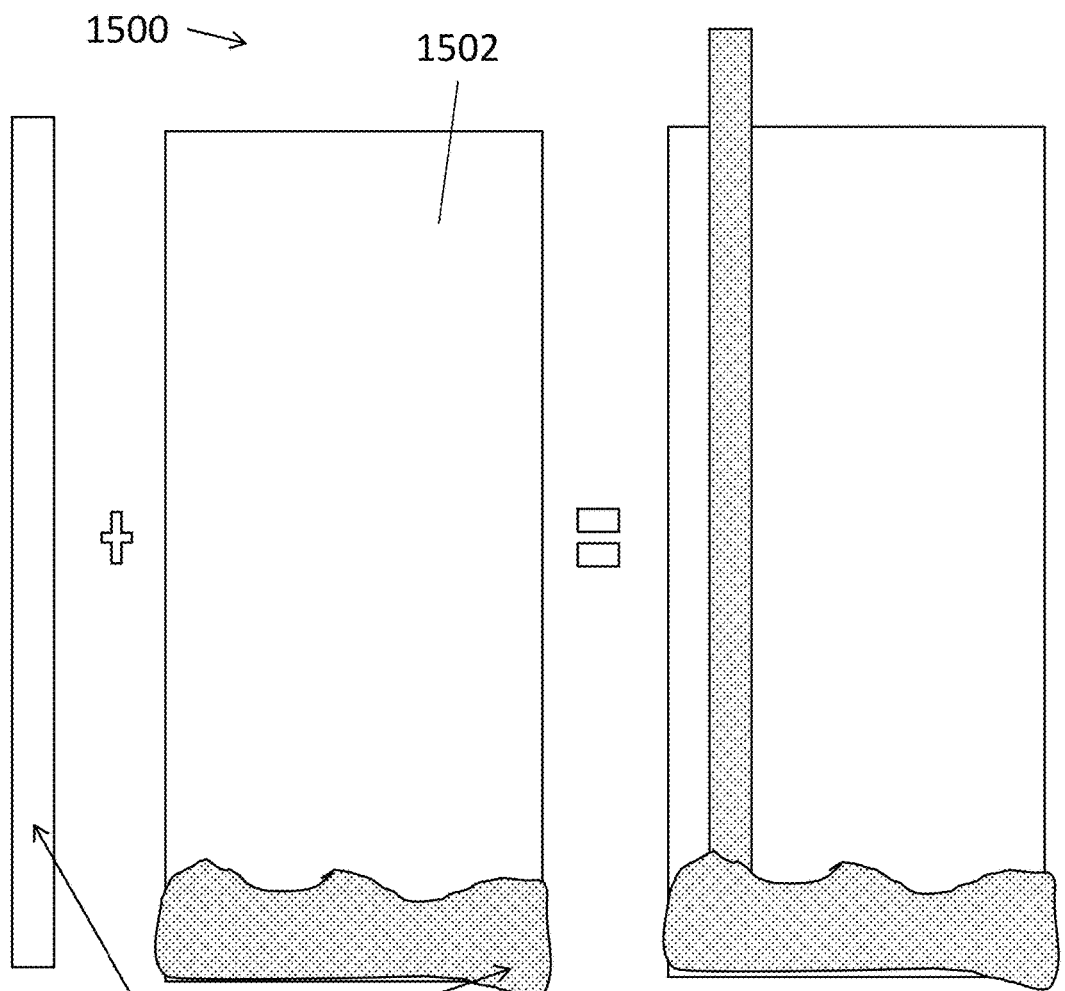
FIGS. 15A-15B illustrate a method of applying hemostatic powder to a nostril to cause blood coagulation in the nostril.
Figure 15B:
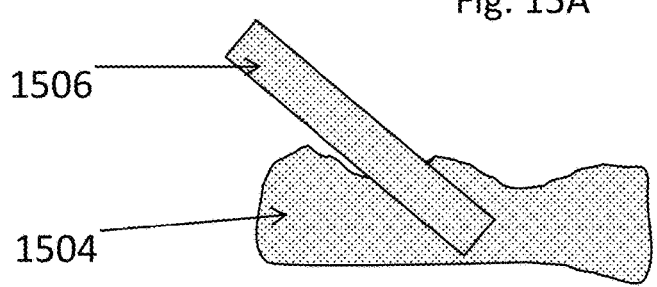

In one embodiment, the invention can include a hemostatic composition administration system 1500 as shown in FIGS. 15A-15B. As shown, the system 1500 includes a package 1502 having a hemostatic composition 1504 and a straw 1506 that is insertable into the package 1502 so as to access the hemostatic composition 1504. While not shown, the straw 1506 can be pointed to pierce the package 1502 and/or the package 1502 can have an opening to receive the straw 1506 therethrough. FIG. 15A shows the straw 1506 placed into the package 1502 so as to access the hemostatic composition 1504. The hemostatic composition 1504 can be sucked or otherwise passed through the straw 1506 for administration. For example, for nasal administration, the nose can be placed on the open end of the straw 1506, and the subject can suck the hemostatic composition 1504 through the straw 1506 by sucking through the nose and thereby through the straw 1506 to drawn the hemostatic composition 1504 through and out from the straw 1506. FIG. 15B shows the hemostatic composition 1504 can be dumped or otherwise removed from the package 1502, and the straw 1506 can be used to sniff or snort the hemostatic composition 1504 for nasal delivery. The hemostatic composition 1504 can be powdered to facilitate the snorting administration through the straw 1506.

Figure 16:
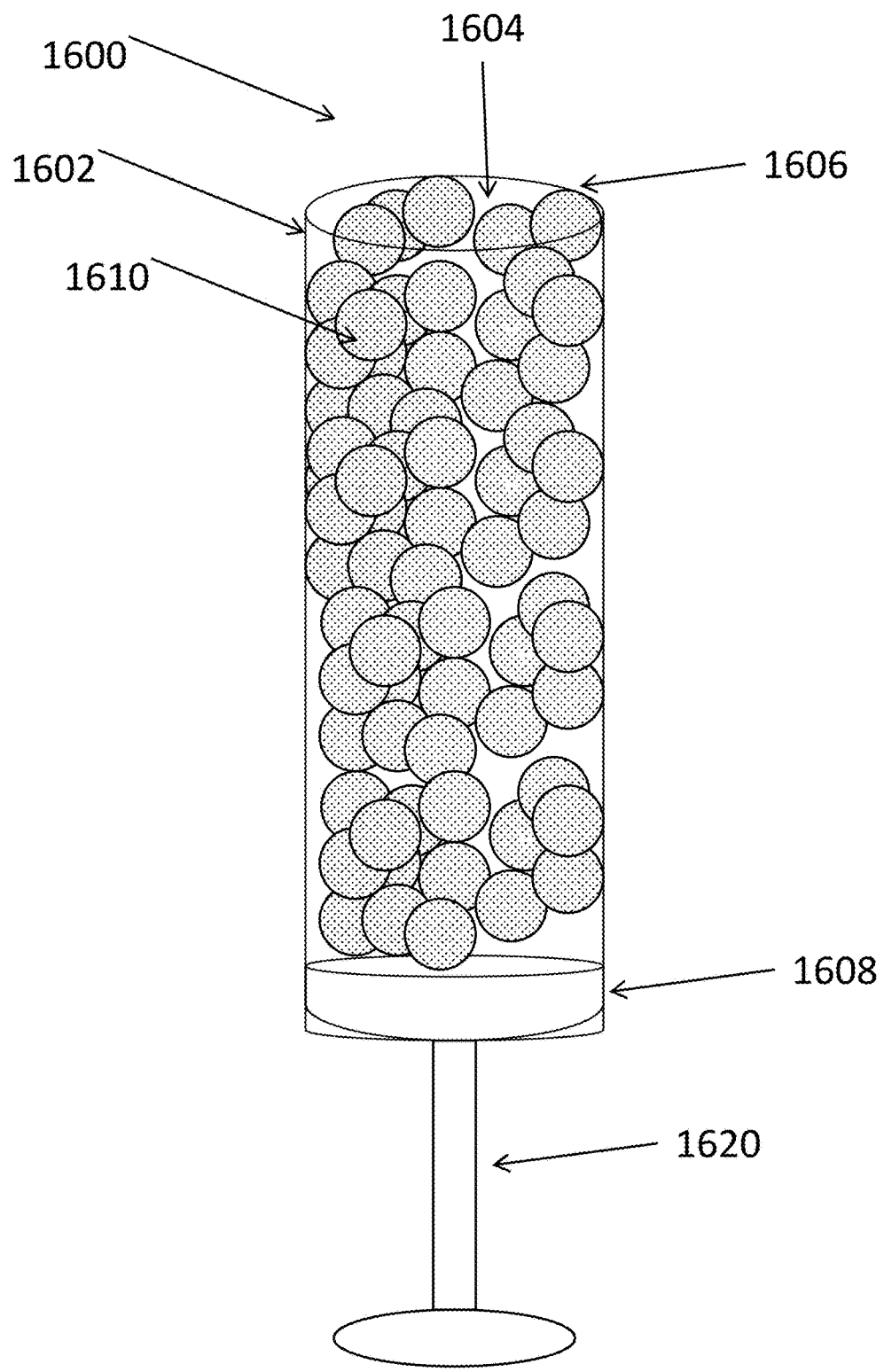
FIG. 16 illustrates an embodiment of an applicator having a plurality of absorbent members, where a plurality of the absorbent members include the hemostatic composition.

FIG. 16 illustrates an embodiment of an applicator 1600 having a plurality of absorbent members 1610, where a plurality of the absorbent members 1610 include the hemostatic composition (e.g., shown by dots) coated on and/or encapsulated in or contained within the absorbent members 1610 in any way. The applicator 1600 includes a body 1602 defining a chamber 1604 having the absorbent members 1610. The applicator 1600 has an open end 1606, or an end that that can be opened. The other end from the opening (e.g., bottom end 1608) has a plunger 1620 that can be pushed to propel the absorbent members 1610 out of the chamber. 1604. The absorbent members 1610 are expandable as they fill with blood or other body liquid. The plurality of absorbent members 1610 can be introduced into a nostril or vagina or wound or any other bleeding area and expanded with blood initially to fill or close off the nostril or vagina or wound or any other bleeding area from leaking or otherwise bleeding more blood and at the same time release the hemostatic composition (e.g., lysine) into the blood to cause coagulation.

In one embodiment, the plurality of hemostatic absorbent particles can meld together from the blood or other body fluid acting as the melding agent. The melding of the particles results in a mass that can be extracted once bleeding has stopped or there is no more flowing blood. Any traditional device or anatomy used to extract subject matter from a nostril, vagina, or wound can be used to withdraw the melded mass of particles once bleeding has stopped flowing out, where fingers and tweezers can be examples.

Also, the plurality of hemostatic absorbent particles allows for only a portion of the particles in the applicator being inserted into the area to stop the blood from flowing out of the area. It may be advantageous to only use a fraction of the total number of particles so that the applicator can be used in a plurality of bleeding instances, preferably the applicator being used multiple times on the same subject. It may be preferable that the applicator is a single subject device and not shared between subjects. However, the ability of multiple injections can provide for a device that is convenient to carry and used selectively on multiple bleeds. For example, subjects with hereditary hemorrhagic telangiectasia (HHT) may experience multiple bleeds in a single day, and a single applicator device that can treat multiple bloods can be advantageous for use and compliance.

Additionally, when the powdered lysine is used to treat the bleed with one or more absorbent members, the powdered lysine can be provided in a way that not all of the powder is contacted to the blood. For example, when an absorbent device has a proximal lysine reservoir that is exposed to the blood, only the top region of lysine may be contacted to the blood; however, the hemostatic properties cause coagulation and a clot to form at the interface with the powder. This allows for the device to be extracted and the powdered lysine pulled away from the clot to leave the clot in place. This is shown by the white centers of the lysine powder that are retained in the images of the figures. See FIGS. 5C, 7A-7B, 8, and 10. These devices were extracted from the nostril while leaving the clot in place.

It was subsequently found that while many commercial nose bleed treatment devices indeed to help to stop nosebleeds, many are difficult to use to get the blood to stop flowing from the nostril and get the hemostatic effect without lying flat or significant tilting back of the head in an attempt to get the nose holes pointing upward. The use of the one or more hemostatic absorbent members allows for application and then allows the subject to be hands-free for the duration of the hemostatic process. Once the clot forms, the one or more absorbent members can be extracted to leave the clot. This is an improvement of hemostatic devices that cling to the clot, which occurs with most hemostatic gauze. Also, devices having a narrow stick with an absorbent end to apply the hemostatic agent were not helpful to stop the blood flow initial as blood easily flowed out the nose without significant pressure applied to stop the flow. Other hemostatic devices had similar problems that did not allow for the subject to have their hands free during the clotting.

However, with the present invention having the one or more hemostatic absorbent members, the absorbent member(s) expand to fill the cavity, such as the nostril or vagina or wound. The expansion is sufficient to stop blood from flowing past and out the cavity. Accordingly, the expansion can be sufficient to apply an outward pressure against the inside surfaces of the cavity, such as in the nose within the opening. The absorption of the blood also allows for the release of the lysine (or other hemostatic agent) into the blood to start the coagulation process. The amount of hemostatic agent can increase in the blood because the blood cannot escape past the absorbent mass blocking off the nostril opening. The result is an increase in concentration in hemostatic agent. When lysine (e.g., powder), the lysine can swamp the protein lysine receptors to promote hemostasis. The formation of the clot is such that the absorbent mass can be pulled away and out without disruption of the clot and causing rebleeding. Rebleeding can be prevented by the lysine diffusing out from the absorbent member and through the blood so that the clot forms outside of the absorbent member and/or device. This allows for a more structurally stable clot or scab to form, which allows for extraction of the absorbent member without rebleeding.

Composition Embodiments

A hemostatic composition for coagulating blood, the hemostatic composition including: a lysine or derivative thereof in an amount sufficient to coagulate blood, optionally in a nasal passageway, wound, surgical site, or vagina. The hemostatic composition of any of the embodiments, wherein the lysine is selected from L-lysine, D-lysine, poly(L-lysine), poly(D-lysine), poly(L,D-lysine), alpha lysine, beta lysine, or combination or derivative thereof. The hemostatic composition of any of the embodiments, wherein the lysine derivative is selected from tranexamic acid, aminocaproic acid, and combination thereof. The hemostatic composition of any of the embodiments, wherein the hemostatic composition is a powder. The hemostatic composition of any of the embodiments, wherein the hemostatic composition is a solid. The hemostatic composition of any of the embodiments, wherein the hemostatic composition is a compressed sheet. The hemostatic composition of any of the embodiments, wherein the hemostatic composition is molded. The hemostatic composition of any of the embodiments, wherein the hemostatic composition is molded into an elongate cylindrical member. The hemostatic composition of any of the embodiments, wherein the hemostatic composition is granular. The hemostatic composition of any of the embodiments, wherein the hemostatic composition includes a microparticle. The hemostatic composition of any of the embodiments, wherein the hemostatic composition includes a nanoparticle. The hemostatic composition of any of the embodiments, comprising another active agent. The hemostatic composition of any of the embodiments, comprising another coagulating or hemostatic substance. The hemostatic composition of any of the embodiments, wherein the lysine or lysine derivative is present in an effective amount to inhibit plasminogen. The hemostatic composition of any of the embodiments, wherein the lysine or lysine derivative is present in an effective amount to inhibit plasminogen conversion to plasmin. The hemostatic composition of any of the embodiments, wherein the lysine or lysine derivative is present in an effective amount to inhibit formation of plasmin. The hemostatic composition of any of the embodiments, wherein the lysine or lysine derivative is present in an effective amount to inhibit fibrinolysis. The hemostatic composition of any of the embodiments, wherein the lysine or lysine derivative is present in an effective amount to occupy a lysine binding site on plasminogen so inhibit conversion to plasmin. The hemostatic composition of any of the embodiments, wherein the lysine or lysine derivative is present in an effective amount to occupy a lysine binding site in a Kringle domain on plasminogen so inhibit conversion to plasmin. The hemostatic composition of any of the embodiments, wherein the lysine or lysine derivative is present in an effective amount to cause blood coagulation on a nasal membrane. The hemostatic composition of any of the embodiments, comprising one or more of excipients, adjuvant, lubricants, pharmaceutically acceptable carrier, flavorant, odorant, absorbent, or the like. The hemostatic composition of any of the embodiments, wherein the hemostatic composition is devoid of at least one of tranexamic acid and aminocaproic acid. The hemostatic composition of any of the embodiments, comprising stearic acid and/or magnesium stearate. The hemostatic composition of any of the embodiments, consisting of lysine. The hemostatic composition of any of the embodiments located in a nasal passageway. The hemostatic composition of any of the embodiments, located on a mucosal membrane in the nasal passageway. The hemostatic composition of any of the embodiments in an aerosoled powder format. The hemostatic composition of any of the embodiments, comprising a plurality of lysine molecules in a powder reservoir. The hemostatic composition of any of the embodiments, the hemostatic composition located on or in a medical device. The hemostatic composition of any of the embodiments, the hemostatic composition located on or in absorbent member. The hemostatic composition of any of the embodiments, the hemostatic composition in a cylindrical member at a first end, the first end being configured for insertion into a nasal passageway. The hemostatic composition of any of the embodiments, comprising an absorbent member forming a container with the lysine or lysine derivative located within the container. The hemostatic composition of any of the embodiments, comprising a memory member having a first compressed shape and a second expanded shape. The hemostatic composition of any of the embodiments, comprising gauze. The hemostatic composition of any of the embodiments, comprising a carrier substrate having the lysine or lysine derivative. The hemostatic composition of any of the embodiments, comprising a hemostatic carrier substrate having the lysine or lysine derivative. The hemostatic composition of any of the embodiments, comprising a mesh hemostatic carrier substrate having the lysine or lysine derivative. The hemostatic composition of any of the embodiments, comprising a foam hemostatic carrier substrate having the lysine or lysine derivative. The hemostatic composition of any of the embodiments, comprising a polymeric hemostatic carrier substrate having the lysine or lysine derivative. The hemostatic composition of any of the embodiments, comprising a cellulosic hemostatic carrier substrate having the lysine or lysine derivative. The hemostatic composition of any of the embodiments, comprising a tissue paper substrate having the lysine or lysine derivative. The hemostatic composition of any of the embodiments, comprising a nutraceutical composition combined with the lysine or lysine derivative. The hemostatic composition of any of the embodiments, comprising a polysaccharide combined with the lysine or lysine derivative. The hemostatic composition of any of the embodiments, the hemostatic composition devoid of a flowable liquid. The hemostatic composition of any of the embodiments, the hemostatic composition comprising a gel. The hemostatic composition of any of the embodiments, the hemostatic composition comprising a paste. The hemostatic composition of any of the embodiments, the hemostatic composition comprising a microsphere. The hemostatic composition of any of the embodiments, the hemostatic composition comprising a nanoparticle. The hemostatic composition of any of the embodiments, the hemostatic composition having less than 500 mg lysine or lysine derivative. The hemostatic composition of any of the embodiments, the hemostatic composition having less than 250 mg lysine or lysine derivative. The hemostatic composition of any of the embodiments, the hemostatic composition having less than 100 mg lysine or lysine derivative. The hemostatic composition of any of the embodiments, the hemostatic composition having less than 50 mg lysine or lysine derivative. The hemostatic composition of any of the embodiments, the hemostatic composition having less than 25 mg lysine or lysine derivative. The hemostatic composition of any of the embodiments, the hemostatic composition having less than 10 mg lysine or lysine derivative. The hemostatic composition of any of the embodiments, the hemostatic composition having less than 5 mg lysine or lysine derivative. The hemostatic composition of any of the embodiments, the hemostatic composition having less than 1 mg lysine or lysine derivative. The hemostatic composition of any of the embodiments, the hemostatic composition having less than 0.5 mg lysine or lysine derivative. The hemostatic composition of any of the embodiments, the hemostatic composition having greater than 500 mg lysine or lysine derivative. The hemostatic composition of any of the embodiments located in a wound. The hemostatic composition of any of the embodiments located in an internal wound. The hemostatic composition of any of the embodiments located in a surgical site. The hemostatic composition of any of the embodiments located in an external wound. The hemostatic composition of any of the embodiments located in a vagina, optionally, before or during menstruation. The hemostatic composition of any of the embodiments located in tooth socket after tooth extraction. The hemostatic composition of any of the embodiments located in a blood outside of a blood vessel. The hemostatic composition of any of the embodiments located in a coagulating blood outside of a blood vessel. The hemostatic composition of any of the embodiments located in a blood clot outside of a blood vessel. The hemostatic composition of any of the embodiments located on a mucosal membrane. The hemostatic composition of any of the embodiments forming a powder cloud. The hemostatic composition of any of the embodiments forming an aerosol.

Device Embodiments

A blood coagulating device comprising: a body; the hemostatic composition of one of the embodiments associated with the body. The device of any of the embodiments, the body including a medical device. The device of any of the embodiments, the body including an absorbent member. The device of any of the embodiments, the body comprising a cylindrical member having a first end having the hemostatic composition, the first end being configured for insertion into a nasal passageway. The device of any of the embodiments, the body being an absorbent hemostatic composition. The device of any of the embodiments, the body comprising a memory member associated with the body, the memory member having a first compressed shape and a second expanded shape. The device of any of the embodiments, the body comprising gauze. The device of any of the embodiments, the body comprising a carrier substrate. The device of any of the embodiments, the body comprising a hemostatic carrier substrate. The device of any of the embodiments, the body comprising a mesh hemostatic carrier substrate. The device of any of the embodiments, the body comprising a foam hemostatic carrier substrate. The device of any of the embodiments, the body comprising a polymeric hemostatic carrier substrate. The device of any of the embodiments, the body comprising a cellulosic hemostatic carrier substrate. The device of any of the embodiments, the body comprising a tissue paper substrate having the lysine or lysine derivative. The device of any of the embodiments, the body comprising a polysaccharide. The device of any of the embodiments, the body having a chamber having the hemostatic composition. The device of one of the embodiments, the body having a surface having the hemostatic composition. The device of any of the embodiments, the body comprising the hemostatic composition embedded therein. The device of any of the embodiments, the body comprising the hemostatic composition thereon. The device of any of the embodiments, the body comprising interstitial spaces having the hemostatic composition. The device of any of the embodiments, the body having one or more depots of the hemostatic composition. The device of any of the embodiments, the body having one or more chamber layers having the hemostatic composition. The device of any of the embodiments, the body being cylindrical. The device of any of the embodiments, the body being tapered from one end to an opposite end. The device of any of the embodiments, the body having a shaped adapted to be received into a nasal passageway. The device of any of the embodiments, the body core and a shell. The device of any of the embodiments, the body having a memory member core with an absorptive shell. The device of any of the embodiments, the body having detachable tab defining at least one side of a chamber having the hemostatic composition. The device of any of the embodiments, the body having a blood-dissolvable portion defining at least one side of a chamber having the hemostatic composition. The device of any of the embodiments, the body having a blood-permeable member defining at least one side of a chamber having the hemostatic composition. The device of any of the embodiments, the body having a blood-impermeable member defining at least one side of a chamber having the hemostatic composition. The device of any of the embodiments, the body having a blood-impermeable member defining at least one side of a chamber having the hemostatic composition, the blood-impermeable member being located at a bottom portion of the body, the bottom portion being opposite of a top portion with respect to the chamber, the top portion being configured to be inserted into a nasal passageway. The device of any of the embodiments, the body having a blood-impermeable member defining at least one side of a chamber having the hemostatic composition, the blood-impermeable member being opposite of a top side with respect to the hemostatic composition. The device of any of the embodiments, the body having a blood-impermeable member defining at least one side surface of the body. The device of any of the embodiments, the body having a blood-impermeable member defining at least one side of a chamber having the hemostatic composition and a blood-permeable member defining at least one side of the chamber. The device of any of the embodiments, the body having a blood-impermeable member defining at least one side of a chamber having the hemostatic composition and a blood-permeable member defining at least one side of the chamber opposite of the blood-impermeable member. The device of any of the embodiments, the body having a blood-impermeable member defining at least one side of a chamber having the hemostatic composition and a blood-permeable member defining at least one side of the chamber. The device of any of the embodiments, the body being a blister package. The device of any of the embodiments, the body having a tear partition. The device of any of the embodiments, the body having an openable seal. The device of any of the embodiments, the body having an airtight chamber having the hemostatic composition therein. The device of any of the embodiments, the body being a unitary member. The device of any of the embodiments, the body comprising multiple members. The device of any of the embodiments, the body being located in an airtight chamber of a package. The device of any of the embodiments, the body having a blood-absorptive portion and a blood-non-absorptive portion, the hemostatic composition being associated with the blood-absorptive portion. The device of any of the embodiments, the body having a blood-absorptive portion that includes a memory member and a blood-non-absorptive portion, the hemostatic composition being associated with the blood-absorptive portion. The device of any of the embodiments, the body having a blood-absorptive portion and a blood-non-absorptive portion, the hemostatic composition being associated with the blood-absorptive portion and the blood-non-absorptive portion. The device of any of the embodiments, the body having a blood-absorptive portion and a blood-non-absorptive portion, the hemostatic composition being between the blood-absorptive portion and blood-non-absorptive portion. The device of any of the embodiments, the body comprising a burst chamber that contains the hemostatic composition. The device of any of the embodiments, the body comprising a burst chamber that contains the hemostatic composition, the burst chamber being configured to burst open at one end of a longitudinal axis upon receiving force or pressure from a lateral axis. The device of any of the embodiments, the body comprising a burst chamber that contains the hemostatic composition, the burst chamber being configured to bust through an opening upon the burst chamber being compressed. The device of any of the embodiments, the body comprising a burst chamber located in an end of an absorbent member, the burst chamber containing the hemostatic composition and being configured to spray the hemostatic composition upon bursting the burst chamber. The device of any of the embodiments, the body comprising a burst chamber that contains the hemostatic composition, the burst chamber being configured to burst open at one end upon being exposed to blood. The device of any of the embodiments, the body comprising a burst chamber that contains the hemostatic composition, the burst chamber being configured to burst open at one end of a longitudinal axis upon receiving force or pressure from a lateral axis. The device of any of the embodiments, wherein the hemostatic composition is released from an end or opening upon the burst chamber bursting. The device of any of the embodiments, the body comprising a pressurized chamber that contains the hemostatic composition, the pressurized chamber being configured to release the hemostatic composition through an opening upon being depressurized. The device of any of the embodiments, the body comprising a pressurized chamber that contains the hemostatic composition, the pressurized chamber being configured to release the hemostatic composition through an opening upon being depressurized by a depressurization device. The device of any of the embodiments, comprising a trigger mechanism operably coupled to the pressurized chamber such that actuation of the trigger mechanism releases the hemostatic composition through an opening. The device of any of the embodiments, comprising a pump operably coupled to a chamber having the hemostatic composition, the pump being adapted to spray the hemostatic composition upon being operated. The device of any of the embodiments, comprising a pump operably coupled to a chamber having the hemostatic composition, the pump being adapted to spray the hemostatic composition as a powder. The device of any of the embodiments, comprising a pump operably coupled to a chamber having the hemostatic composition, the pump being adapted to spray the hemostatic composition as powdered dry particles, optionally, the pump includes a bulb that has an internal chamber with the hemostatic composition and that sprays the dry hemostatic composition particles upon being squeezed. The device of any of the embodiments, the body comprising an absorbent member located in a burst chamber, wherein the absorbent member can be extracted from the burst chamber upon bursting and inserted in a nasal passageway, optionally, the bursting can spray the hemostatic composition into the nose, and then the absorbent member having the hemostatic composition can be withdrawn from the burst chamber and inserted into the nasal passageway. The device of any of the embodiments, the body having the hemostatic composition sprinkled on an outer surface, the hemostatic composition being powdered and capable of being removed. The device of any of the embodiments, the body having receptacles for the powdered hemostatic composition on an outer surface, such that the powder can be rubbed or sprinkled off. The device of any of the embodiments, comprising a spray mechanism associated with a chamber having the hemostatic composition, the spray mechanism being capable of spraying the hemostatic composition from the chamber. The device of any of the embodiments, comprising a spray mechanism associated with a chamber having the hemostatic composition, the spray mechanism being capable of spraying the hemostatic composition from the chamber, wherein the spray chamber is a burst chamber with or without the hemostatic composition and the chamber sprays the hemostatic composition by bursting the burst chamber. The device of any of the embodiments, wherein the hemostatic composition is a different composition that may or may not have lysine or lysine derivative, optionally the composition includes an active agent. The device of any of the embodiments, the device configured to deliver the hemostatic composition to a nasal passageway. The device of any of the embodiments, the device configured to spray the hemostatic composition into a nasal passageway. The device of any of the embodiments, the device configured to aerosol the hemostatic composition into a nasal passageway. The device of any of the embodiments, the device configured to apply the hemostatic composition into a membrane of a nasal passageway. The device of any of the embodiments, the device configured to contact the hemostatic composition into a membrane of a nasal passageway. The device of any of the embodiments, the device configured to spray the hemostatic composition into blood in a bleeding nasal passageway. The device of any of the embodiments, the device configured to contact the hemostatic composition to blood in a bleeding nasal passageway outside of a blood vessel. The device of any of the embodiments, the device configured to absorb blood until the blood contacts the hemostatic composition, the blood being from into a bleeding nasal passageway. The device of any of the embodiments, the body being configured a nose plug. The device of any of the embodiments, the body being configured a nose plug configured to block blood flow. The device of any of the embodiments, the body being biodegradable. The device of any of the embodiments, the body being biostable. The device of any of the embodiments, the body being blood-stable so as to retain its integrity when exposed to blood. The device of any of the embodiments, the body being blood-degradable so as degrade and expose the hemostatic composition to the blood upon contact with the blood. The device of any of the embodiments, the body including hydroxyethylcellulose and/or amylopectin. A device for coagulating blood in a nasal passageway, comprising the device of one of the embodiments configured for insertion into the nose. A device for coagulating blood in a nasal passageway, comprising the device of one of the embodiments configured to spray the hemostatic composition into the nasal passageway. A device for coagulating blood in a nasal passageway, comprising the device of one of the embodiments configured to apply the hemostatic composition to blood in the nasal passageway. A device for coagulating blood in a nasal passageway, comprising the device of one of the embodiments configured to apply the hemostatic composition to a surface of the nasal passageway. A device for coagulating blood in a nasal passageway, comprising the device of one of the embodiments configured to apply the hemostatic composition to a membrane of the nasal passageway. A device for coagulating blood, comprising the device of one of the embodiments configured to apply the hemostatic composition to blood. A device for coagulating blood, comprising the device of one of the embodiments configured to apply the hemostatic composition to a wound. A device for coagulating blood, comprising the device of one of the embodiments configured to apply the hemostatic composition to a vagina during menstruation. A device for coagulating blood, comprising the device of one of the embodiments configured to apply the hemostatic composition to an external wound in skin. A device for coagulating blood, comprising the device of one of the embodiments configured to apply the hemostatic composition to an internal would, the device being blood-stable so as to be capable of being withdrawn from the internal wound intact. A device for coagulating blood, comprising the device of one of the embodiments configured to be inserted into a wound so as to apply the hemostatic composition to blood in the wound. The device of any of the embodiments, the body being a blister pack having the hemostatic composition therein. The device of any of the embodiments, the body being in a contracted form and having an expanded form upon contact with liquid, such as blood. The device of any of the embodiments, the body being blood-expandable from a first smaller size to a second larger size upon exposure to blood. The device of any of the embodiments, the body having a recess at a first end, the recess having the hemostatic composition, the first end being adapted to be inserted into a nasal passageway. The device of any of the embodiments, the body having a recess at a first end, the recess having the hemostatic composition, a removable cover over the recess in the first end, the first end being adapted to be inserted into a nasal passageway. The device of any of the embodiments, the body having a recess at a first end, the recess having the hemostatic composition, a blood-degradable cover over the recess in the first end, the first end being adapted to be inserted into a nasal passageway. The device of any of the embodiments, the body having a recess at a first end, the recess having the hemostatic composition, a blood-permeable cover over the recess in the first end, the first end being adapted to be inserted into a nasal passageway. The device of any of the embodiments, the body having a recess at a first end, the recess having the hemostatic composition, a tear-off cover over the recess in the first end, the first end being adapted to be inserted into a nasal passageway. The device of any of the embodiments, the body having a recess at a first end, the recess having the hemostatic composition, an openable cover over the recess in the first end, the openable cover being configured to be opened to expose the hemostatic composition, the first end being adapted to be inserted into a nasal passageway. The device of any of the embodiments, the body comprising sprinkle apertures coupled to a reservoir having the hemostatic composition, the hemostatic composition being capable of sprinkling from the sprinkle apertures.

Coagulation Method Embodiments

A method for coagulating blood, the method comprising: providing the hemostatic composition of one of the embodiments; and applying the hemostatic composition to blood so as to cause the blood to coagulate. In one embodiment, the blood being outside of a blood vessel. In one embodiment, the blood being outside of a blood vessel in a body cavity, such as a nostril or vagina. In one embodiment, the hemostatic composition being applied outside and away from the bleeding blood vessel, such as in the nostril or vagina away from the blood vessel. The method of any of the embodiments, comprising spraying the hemostatic composition onto blood. The method of any of the embodiments, comprising spraying the hemostatic composition into blood. The method of any of the embodiments, comprising spraying the hemostatic composition onto a nasal passageway. The method of any of the embodiments, comprising spraying the hemostatic composition onto a wound. The method of any of the embodiments, comprising spraying the hemostatic composition onto a surgical site. The method of any of the embodiments, comprising contacting the hemostatic composition onto blood. The method of any of the embodiments, comprising inserting the hemostatic composition into blood. The method of any of the embodiments, comprising inserting the hemostatic composition onto a nasal passageway. The method of any of the embodiments, comprising inserting the hemostatic composition onto a wound. The method of any of the embodiments, comprising inserting the hemostatic composition onto a surgical site. The method of any of the embodiments, comprising applying the hemostatic composition as a powder. The method of any of the embodiments, comprising applying the hemostatic composition as a gel. The method of any of the embodiments, comprising applying the hemostatic composition as a paste. The method of any of the embodiments, comprising the hemostatic composition being devoid of a liquid. The method of any of the embodiments, comprising the hemostatic composition including a liquid. The method of any of the embodiments, comprising the hemostatic composition being in a liquid format. The method of any of the embodiments, comprising the hemostatic composition being in a fluidic format that is non-liquid. The method of any of the embodiments, comprising the hemostatic composition being a solid. The method of any of the embodiments, comprising the hemostatic composition causing the blood to clot. The method of any of the embodiments, comprising the coagulation occurring in a nasal passageway, wound, surgical site, or vagina. The method of any of the embodiments, comprising coagulating the blood away from a blood vessel. The method of any of the embodiments, comprising coagulating the blood at or in a blood vessel. The method of any of the embodiments, comprising causing coagulation at a ruptured blood vessel so as to induce healing of the ruptured blood vessel. The method of any of the embodiments, comprising coagulating blood within a nasal passageway so as to inhibit the blood from flowing. The method of any of the embodiments, comprising inhibiting blood from flowing from a nasal passageway. The method of any of the embodiments, comprising applying the hemostatic composition via the device of one of the embodiments. The method of any of the embodiments, comprising releasing the hemostatic composition from the device. The method of any of the embodiments, comprising spraying the hemostatic composition from the device. The method of any of the embodiments, comprising aerosolizing the hemostatic composition from the device. The method of any of the embodiments, comprising squeezing the device so as to release the hemostatic composition therefrom. The method of any of the embodiments, comprising activating a mechanism in the device so as to release the hemostatic composition therefrom. The method of any of the embodiments, comprising smearing, rubbing, or otherwise contacting the hemostatic composition to blood or a mucus membrane having blood thereon. The method of any of the embodiments, comprising providing a device having the hemostatic composition. The method of any of the embodiments, comprising: providing a device having the hemostatic composition; and applying the device to the blood so that the hemostatic composition causes the blood to coagulate. The method of any of the embodiments, comprising providing the hemostatic composition to the device. The method of any of the embodiments, comprising applying the lysine or lysine derivative to blood in an effective amount to inhibit plasminogen. The method of any of the embodiments, comprising applying the lysine or lysine derivative in an effective amount to inhibit plasminogen conversion to plasmin in the blood. The method of any of the embodiments, comprising applying the lysine or lysine derivative in an effective amount to inhibit formation of plasmin. The method of any of the embodiments, comprising applying the lysine or lysine derivative in an effective amount to inhibit fibrinolysis. The method of any of the embodiments, comprising applying the lysine or lysine derivative in an effective amount to occupy a lysine binding site on plasminogen so inhibit conversion to plasmin. The method of any of the embodiments, comprising applying the lysine or lysine derivative in an effective amount to occupy a lysine binding site in a Kringle domain on plasminogen so inhibit conversion to plasmin. The method of any of the embodiments, comprising applying the lysine or lysine derivative in an effective amount to cause blood coagulation on a nasal membrane. The method of any of the embodiments, comprising applying the lysine or lysine derivative so as to be located in a nasal passageway. The method of any of the embodiments, comprising applying the lysine or lysine derivative so as to be located on a mucosal membrane in the nasal passageway. The method of any of the embodiments, comprising applying the lysine or lysine derivative in an aerosoled powder format. The method of any of the embodiments, comprising applying the lysine or lysine derivative as a plurality of lysine molecules in a powder reservoir. The method of any of the embodiments, comprising applying the lysine or lysine derivative to blood from a medical device. The method of any of the embodiments, comprising applying the lysine or lysine derivative to blood from an absorbent member. The method of any of the embodiments, comprising applying the lysine or lysine derivative to blood from in a cylindrical member at a first end, the first end being configured for insertion into a nasal passageway or vagina. The method of any of the embodiments, comprising releasing a memory member from a first compressed shape and a second expanded shape in a nasal passageway, wound, surgical site, or vagina, the memory member being in a device having the hemostatic composition.

Method of Manufacturing Device Embodiments

A method of manufacturing a blood coagulating device comprising: forming a body; and associating a hemostatic composition with the body, the hemostatic composition being of one of the embodiments. The method of any of the embodiments, comprising forming the body to include a medical device. The method of any of the embodiments, comprising forming the body to include an absorbent member. The method of any of the embodiments, comprising forming the body to include a cylindrical member having a first end having the hemostatic composition, the first end being configured for insertion into a nasal passageway. The method of any of the embodiments, comprising forming the absorbent member. The method of any of the embodiments, comprising forming the body to include a memory member associated with the body, the memory member having a first compressed shape and a second expanded shape. The method of any of the embodiments, comprising forming the body to include gauze. The method of any of the embodiments, comprising forming the body to include a carrier substrate. The method of any of the embodiments, comprising forming the body to comprise a hemostatic carrier substrate. The method of any of the embodiments, comprising forming the body to comprise a mesh hemostatic carrier substrate. The method of any of the embodiments, comprising forming the body to comprise a foam hemostatic carrier substrate. The method of any of the embodiments, comprising forming the body to comprise a polymeric hemostatic carrier substrate. The method of any of the embodiments, comprising forming the body to comprise a cellulosic hemostatic carrier substrate. The method of any of the embodiments, comprising forming the body to comprise a tissue paper substrate having the lysine or lysine derivative. The method of any of the embodiments, comprising forming the body to comprise a polysaccharide. The method of any of the embodiments, comprising forming the body to have a chamber having the hemostatic composition. The method of one of the embodiments, comprising forming the body to have a surface having the hemostatic composition. The method of any of the embodiments, comprising forming the body to comprise the hemostatic composition embedded therein. The method of any of the embodiments, comprising forming the body to comprise the hemostatic composition thereon. The method of any of the embodiments, comprising forming the body to comprise interstitial spaces having the hemostatic composition. The method of any of the embodiments, comprising forming the body to have one or more depots of the hemostatic composition. The method of any of the embodiments, comprising forming the body to have one or more chamber layers having the hemostatic composition. The method of any of the embodiments, comprising forming the body to be cylindrical. The method of any of the embodiments, comprising forming the body to be tapered from one end to an opposite end. The method of any of the embodiments, comprising forming the body to have a shaped adapted to be received into a nasal passageway. The method of any of the embodiments, comprising forming the body to have a core and a shell. The method of any of the embodiments, comprising forming the body to have a memory member core with an absorptive shell. The method of any of the embodiments, comprising forming the body to have a detachable tab defining at least one side of a chamber having the hemostatic composition. The method of any of the embodiments, comprising forming the body to have a blood-dissolvable portion defining at least one side of a chamber having the hemostatic composition. The method of any of the embodiments, comprising forming the body to have a blood-permeable member defining at least one side of a chamber having the hemostatic composition. The method of any of the embodiments, comprising forming the body to have a blood-impermeable member defining at least one side of a chamber having the hemostatic composition. The method of any of the embodiments, comprising forming the body to have a blood-impermeable member defining at least one side of a chamber having the hemostatic composition, the blood-impermeable member being located at a bottom portion of the body, the bottom portion being opposite of a top portion with respect to the chamber, the top portion being configured to be inserted into a nasal passageway. The method of any of the embodiments, comprising forming the body to have a blood-impermeable member defining at least one side of a chamber having the hemostatic composition, the blood-impermeable member being opposite of a top side with respect to the hemostatic composition. The method of any of the embodiments, comprising forming the body to have a blood-impermeable member defining at least one side surface of the body. The method of any of the embodiments, comprising forming the body to have a blood-impermeable member defining at least one side of a chamber having the hemostatic composition and a blood-permeable member defining at least one side of the chamber. The method of any of the embodiments, comprising forming the body to have a blood-impermeable member defining at least one side of a chamber having the hemostatic composition and a blood-permeable member defining at least one side of the chamber opposite of the blood-impermeable member. The method of any of the embodiments, comprising forming the body to have a blood-impermeable member defining at least one side of a chamber having the hemostatic composition and a blood-permeable member defining at least one side of the chamber. The method of any of the embodiments, comprising forming the body to be a blister package. The method of any of the embodiments, comprising forming the body to have a tear partition. The method of any of the embodiments, comprising forming the body to have an openable seal. The method of any of the embodiments, comprising forming the body to have an airtight chamber having the hemostatic composition therein. The method of any of the embodiments, comprising forming the body to be a unitary member. The method of any of the embodiments, comprising forming the body to comprise multiple members. The method of any of the embodiments, comprising locating the body in an airtight chamber of a package. The method of any of the embodiments, comprising forming the body to have a blood-absorptive portion and a blood-non-absorptive portion, the hemostatic composition being associated with the blood-absorptive portion. The method of any of the embodiments, comprising forming the body to have a blood-absorptive portion that includes a memory member and a blood-non-absorptive portion, the hemostatic composition being associated with the blood-absorptive portion. The method of any of the embodiments, comprising forming the body to have a blood-absorptive portion and a blood-non-absorptive portion, the hemostatic composition being associated with the blood-absorptive portion and the blood-non-absorptive portion. The method of any of the embodiments, comprising forming the body to have a blood-absorptive portion and a blood-non-absorptive portion, the hemostatic composition being between the blood-absorptive portion and blood-non-absorptive portion. The method of any of the embodiments, comprising forming the body to comprise a burst chamber that contains the hemostatic composition. The method of any of the embodiments, comprising forming the body to comprise a burst chamber that contains the hemostatic composition, the burst chamber being configured to burst open at one end of a longitudinal axis upon receiving force or pressure from a lateral axis. The method of any of the embodiments, comprising forming the body to comprise a burst chamber that contains the hemostatic composition, the burst chamber being configured to bust through an opening upon the burst chamber being compressed. The method of any of the embodiments, comprising forming the body to comprise a burst chamber located in an end of an absorbent member, the burst chamber containing the hemostatic composition and being configured to spray the hemostatic composition upon bursting the burst chamber. The method of any of the embodiments, comprising forming the body to comprise a burst chamber that contains the hemostatic composition, the burst chamber being configured to burst open at one end upon being exposed to blood. The method of any of the embodiments, comprising forming the body to comprise a burst chamber that contains the hemostatic composition, the burst chamber being configured to burst open at one end of a longitudinal axis upon receiving force or pressure from a lateral axis. The method of any of the embodiments, comprising forming the device with a burst chamber such that the hemostatic composition is released from an end or opening upon the burst chamber bursting. The method of any of the embodiments, comprising forming the body to comprise a pressurized chamber that contains the hemostatic composition, the pressurized chamber being configured to release the hemostatic composition through an opening upon being depressurized. The method of any of the embodiments, comprising the body to comprise a pressurized chamber that contains the hemostatic composition, the pressurized chamber being configured to release the hemostatic composition through an opening upon being depressurized by a depressurization device. The method of any of the embodiments, comprising coupling a trigger mechanism to the pressurized chamber such that actuation of the trigger mechanism releases the hemostatic composition through an opening. The method of any of the embodiments, comprising coupling a pump to a chamber having the hemostatic composition, the pump being adapted to spray the hemostatic composition upon being operated. The method of any of the embodiments, comprising coupling a pump to a chamber having the hemostatic composition, the pump being adapted to spray the hemostatic composition as a powder. The method of any of the embodiments, comprising coupling a pump to a chamber having the hemostatic composition, the pump being adapted to spray the hemostatic composition as powdered dry particles, optionally, the pump includes a bulb (e.g., turkey baster bulb) that has an internal chamber with the hemostatic composition and that sprays the dry hemostatic composition particles upon being squeezed. The method of any of the embodiments, comprising forming an absorbent member and located the absorbent member in a burst chamber, wherein the absorbent member can be extracted from the burst chamber upon bursting and inserted in a nasal passageway, optionally, the bursting can spray the hemostatic composition into the nose, and then the absorbent member having the hemostatic composition can be withdrawn from the burst chamber and inserted into the nasal passageway. The method of any of the embodiments, comprising forming the body to have the hemostatic composition sprinkled on an outer surface, the hemostatic composition being powdered and capable of being removed. The method of any of the embodiments, comprising forming the body to have receptacles in an outer surface and locating the powdered hemostatic composition in the receptacles in the outer surface, such that the powder can be rubbed or sprinkled off the body. The method of any of the embodiments, comprising coupling a spray mechanism with a chamber having the hemostatic composition, the spray mechanism being capable of spraying the hemostatic composition from the chamber. The method of any of the embodiments, comprising coupling a spray mechanism with a chamber having the hemostatic composition, the spray mechanism being capable of spraying the hemostatic composition from the chamber, wherein the spray chamber is a burst chamber with or without the hemostatic composition and the chamber sprays the hemostatic composition by bursting the burst chamber. The method of any of the embodiments, comprising preparing a hemostatic composition that is a different hemostatic composition that may or may not have lysine or lysine derivative, optionally the hemostatic composition includes an active agent, and combining the different hemostatic composition with the body, where the hemostatic composition having lysine may or may not be combined with the body (e.g., that is, the device can include any other nutraceutical and/or pharmaceutical hemostatic composition that may or may not have lysine or lysine derivative). The method of any of the embodiments, comprising configuring the device so as to deliver the hemostatic composition to a nasal passageway. The method of any of the embodiments, wherein the device is configured to spray the hemostatic composition into a nasal passageway. The method of any of the embodiments, wherein the device is configured to aerosol the hemostatic composition into a nasal passageway. The method of any of the embodiments, wherein the device is configured to apply the hemostatic composition into a membrane of a nasal passageway. The method of any of the embodiments, wherein the device is configured to contact the hemostatic composition to a membrane of a nasal passageway. The method of any of the embodiments, wherein the device is configured to spray the hemostatic composition into blood in a bleeding nasal passageway. The method of any of the embodiments, wherein the device configured to contact the hemostatic composition to blood in a bleeding nasal passageway. The method of any of the embodiments, wherein the device is configured to absorb blood until the blood contacts the hemostatic composition, the blood being from into a bleeding nasal passageway. The method of any of the embodiments, wherein the body is configured as a nose plug. The method of any of the embodiments, wherein the body is configured a nose plug configured to block blood flow. The method of any of the embodiments, comprising forming the body to be biodegradable. The method of any of the embodiments, comprising forming the body to be biostable. The method of any of the embodiments, comprising forming the body to be blood-stable so as to retain its integrity when exposed to blood. The method of any of the embodiments, comprising forming the body to be blood-degradable so as degrade and expose the hemostatic composition to the blood upon contact with the blood. The method of any of the embodiments, comprising forming the body to include hydroxyethylcellulose and/or amylopectin. The method of any of the embodiments, comprising forming the device for insertion into the nose. The method of any of the embodiments, comprising forming the device to spray the hemostatic composition into the nasal passageway. The method of any of the embodiments, comprising forming the device to apply the hemostatic composition to blood in the nasal passageway. The method of any of the embodiments, comprising forming the device to apply the hemostatic composition to a surface of the nasal passageway. The method of any of the embodiments, comprising forming the device to apply the hemostatic composition to a membrane of the nasal passageway. The method of any of the embodiments, comprising forming the device to apply the hemostatic composition to blood. The method of any of the embodiments, comprising forming the device to apply the hemostatic composition to a wound. The method of any of the embodiments, comprising forming the device to apply the hemostatic composition to a vagina before or during menstruation. The method of any of the embodiments, comprising forming the device to apply the hemostatic composition to an external wound in skin. The method of any of the embodiments, comprising forming the device to apply the hemostatic composition to an internal wound, the device being blood-stable so as to be capable of being withdrawn from the internal wound intact. The method of any of the embodiments, comprising forming the device to be inserted into a wound so as to apply the hemostatic composition to blood in the wound. The method of any of the embodiments, comprising forming the body to be a blister pack having the hemostatic composition therein. The method of any of the embodiments, comprising forming the body to be in a contracted form and having an expanded form upon contact with liquid, such as blood. The method of any of the embodiments, comprising forming the body to be blood-expandable from a first smaller size to a second larger size upon exposure to blood. The method of any of the embodiments, comprising forming the body to have a recess at a first end, the recess having the hemostatic composition, the first end being adapted to be inserted into a nasal passageway. The method of any of the embodiments, comprising forming the body to have a recess at a first end, the recess having the hemostatic composition, applying a removable cover over the recess in the first end, the first end being adapted to be inserted into a nasal passageway. The method of any of the embodiments, comprising forming the body to have a recess at a first end, the recess having the hemostatic composition, applying a blood-degradable cover over the recess in the first end, the first end being adapted to be inserted into a nasal passageway. The method of any of the embodiments, comprising forming the body to have a recess at a first end, the recess having the hemostatic composition, applying a blood-permeable cover over the recess in the first end, the first end being adapted to be inserted into a nasal passageway. The method of any of the embodiments, comprising forming the body to have a recess at a first end, the recess having the hemostatic composition, forming a tear-off cover over the recess in the first end, the first end being adapted to be inserted into a nasal passageway. The method of any of the embodiments, comprising forming the body to have a recess at a first end, the recess having the hemostatic composition, forming an openable cover over the recess in the first end, the openable cover being configured to be opened to expose the hemostatic composition, the first end being adapted to be inserted into a nasal passageway. The method of any of the embodiments, comprising: obtaining a substrate; applying the hemostatic composition to a first surface of the substrate; folding the substrate so that a first portion of the first surface of substrate contacts a second portion of the first surface of the substrate; and fastening the first portion to the second portion. The method of embodiment, comprising adhering the first portion to the second portion. The method of any of embodiments, comprising rolling the folded substrate into a cylindrical form. The method of any of embodiments, comprising applying the hemostatic composition into a crease in the substrate and folding the substrate at the crease so that the hemostatic composition is at an end or edge of the device. The method of any of embodiments, wherein the fastening is adhering. The method of any of embodiments, comprising applying an adhesive to a second surface of the substrate such that rolling the substrate forms a cylindrical member. The method of any of embodiments, wherein the hemostatic composition is located in a plurality of layers of the rolled substrate. The method of any of embodiments, comprising forming a tear portion that when torn opens the device to expose the hemostatic composition. The method of any of the embodiments, forming sprinkle apertures in a device, the sprinkle apertures fluidly coupling with a reservoir having the hemostatic composition such that the hemostatic composition can be sprinkled from the sprinkle apertures.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

EXPERIMENTAL

Figure 3:
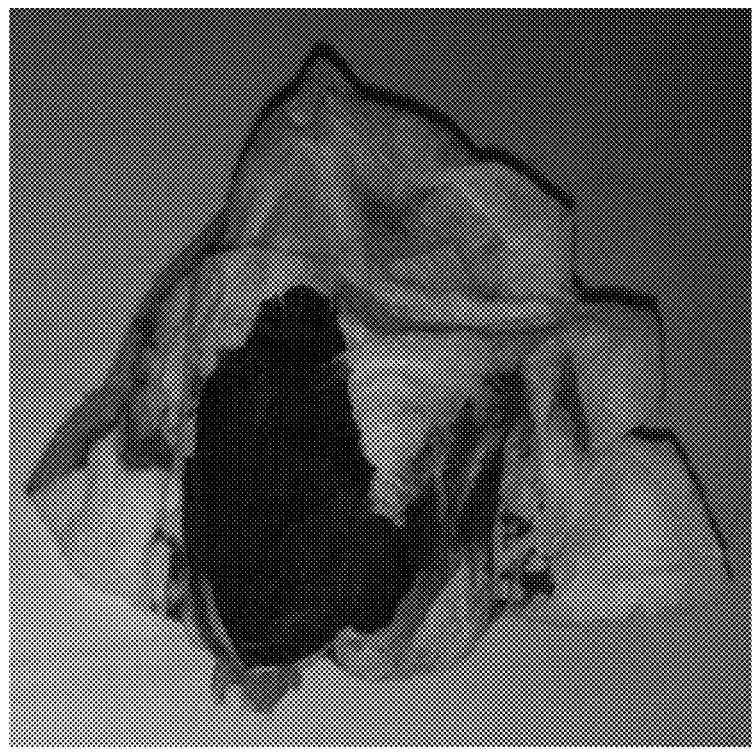
FIG. 3 is an image of tissue without a hemostatic composition.

As a control, regular tissue and regular gauze were used to treat a nose bleed by rolling or otherwise fashioning a nose plug from the materials, and no lysine was added. The tissues and gauze appear to absorb the blood, but the blood continues to flow. In some instances, the blood flow can be significant and require a large number of sequential tissues or gauze. Nose bleeds treated with tissues can last 10 minutes or more up to an hour or longer when the bleed is significant. In some instances a nose bleed can be from both nostrils and both nostrils have to be plugged with a nose plug. The tissues and gauze do not appear to be promoting clotting. FIG. 3 shows an image of a tissue without lysine that is saturated with blood.

Figure 4:
FIG. 4 is an image of an absorbent member having a hemostatic composition.

When a 5-500 mg lysine hemostatic composition is applied to tissue, the lysine interacts with the blood and promotes clotting when the tissue is used to treat a nose bleed. The nose bleed often stops within 1 minute when the tissue includes lysine, compared a long period when only tissues are used. A significant bleed was stopped within 5 minutes when lysine was included in the gauze. The image of FIG. 4 shows a tissue having the lysine hemostatic composition therein, where the blood is less absorbed and lysine powder is still present. Available lysine was present after the nose bleed was treated to stop blood flow. The lysine powder is still in a powder format after bleeding is stopped, which indicates that lysine is absorbed into the blood and causes the coagulation such that when the tissue is withdrawn, the un-used powder is still present. Accordingly, substantially less than 500 mg lysine (E.g., 5 mg) is needed to stop bleeding in a short time. The device including the tissue and the lysine powder is able to be withdrawn with the blood no longer flowing through the nose.

Figure 5A:
FIGS. 5A-5D include images of hemostatic gauze absorbent members having hemostatic compositions.
Figure 5B:
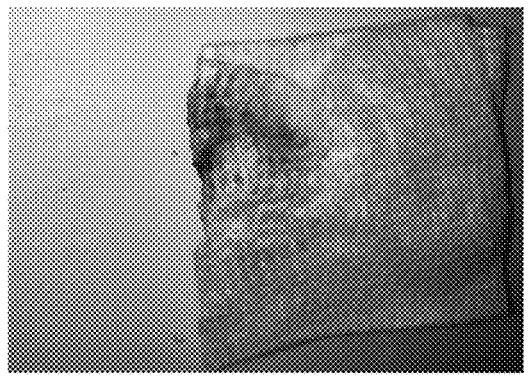
Figure 5C:
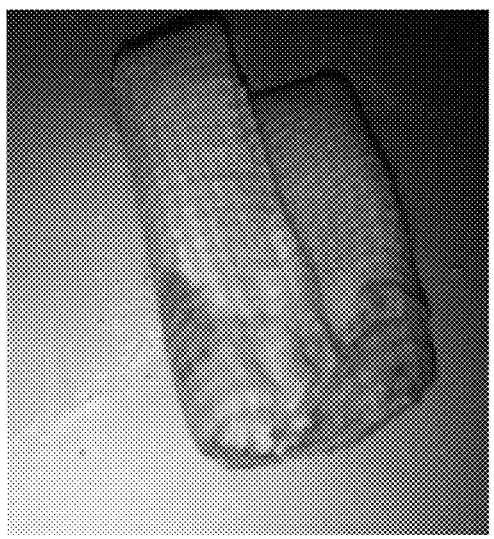
Figure 5D:
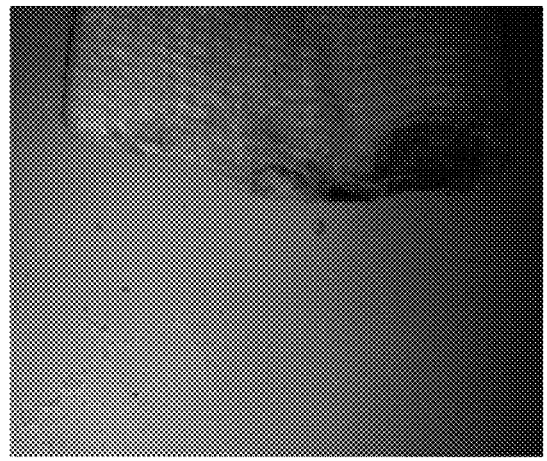

The images of FIGS. 5A-5D show that a gauze (regenerated etherized and oxidized natural fiber cellulose—Walgreens Blood Barrier Hemostat gauze) having about 250 mg lysine powder didn't absorb much blood, where the nose bleed stopped within a minute. The bleed was a slower bleed, but the lysine was effective in quickly stopping the blood flow so that the gauze could be removed in short time (just over a minute). Additionally, there was still excess powder. The gauze was rolled up with the lysine powder at one end, and the lysine powder was inserted into the nose, then the gauze was released and allowed to expand and plug the nose. FIG. 5A shows the length of blood absorption in the rolled device. FIG. 5B shows another examples of a device unrolled to show length of blood absorption. FIG. 5C shows the device having the receptacle at the end with the lysine hemostatic composition and blood length absorption. FIG. 5D shows another example with low blood absorption penetration when lysine is included.

Figure 6:
FIG. 6 is an image showing a control tissue against a lysine tissue and two lysine gauzes (e.g., regenerated etherized and oxidized natural fiber cellulose).

FIG. 6 includes a control tissue against a lysine tissue and two lysine gauze (regenerated etherized and oxidized natural fiber cellulose). The tissue without lysine is clearly more saturated with blood and the tissue didn't stop the blood from flowing in the nostril and out. The lysine tissue absorbed less blood, and the blood flow was stopped in the nostril. The lysine gauze absorbed less blood, however, the lysine was placed at the end and was more accessible to the blood. Whereas the lysine tissue had the lysine rolled in the tissue rolls. The nose quite bleeding quickly with the lysine tissue and lysine gauze.

Figure 7A:
FIGS. 7A-7B is an image that show an example of a lysine gauze with a heavy nose bleed, where the gauze absorbed a significant amount of blood and the lysine center, which can be seen as the white center, still had lysine available.
Figure 7B:

FIGS. 7A-7B show an example of a lysine gauze with a heavy nose bleed, where the gauze absorbed a significant amount of blood and the lysine center, which can be seen as the white center, still had lysine available. The blood stopped flowing from the nose within 2 minutes with the lysine gauze, and stopped the flow significantly faster that when without the lysine.

Figure 10:
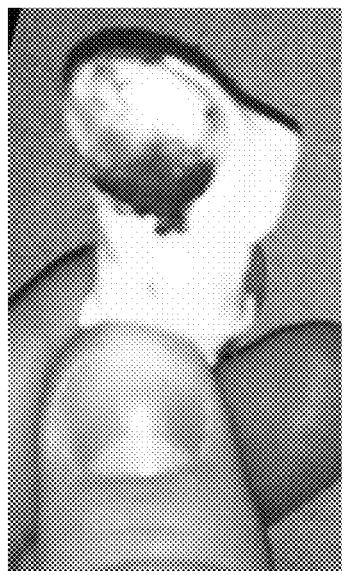
FIG. 10 is an image that shows a rolled lysine tissue device, where the lysine stopped the bleed quickly, as little blood is absorbed into the tissue, and where the lysine was in a recess at the end, and there is still fresh lysine powder that has not contacted blood.

FIG. 8 shows a lysine tissue with the lysine being in a receptacle at the end that is inserted in the nostril. The absorbent material of the tissue shows the blood absorbed on the outside, but again shows the white center of the lysine. This shows the lysine is coagulating the blood and stopping the flow. The lysine is able to be withdrawn and reveal a clean edge showing the blood is not flowing. FIG. 9A shows a rolled tissue device having a receptacle at the end empty, and FIG. 9B shows the receptacle filed with lysine powder. FIG. 10 shows a rolled lysine tissue device, were the lysine stopped the bleed quickly, as little is absorbed into the tissue. The lysine was in a recess at the end, and you can still see fresh lysine powder.

Figure 11:
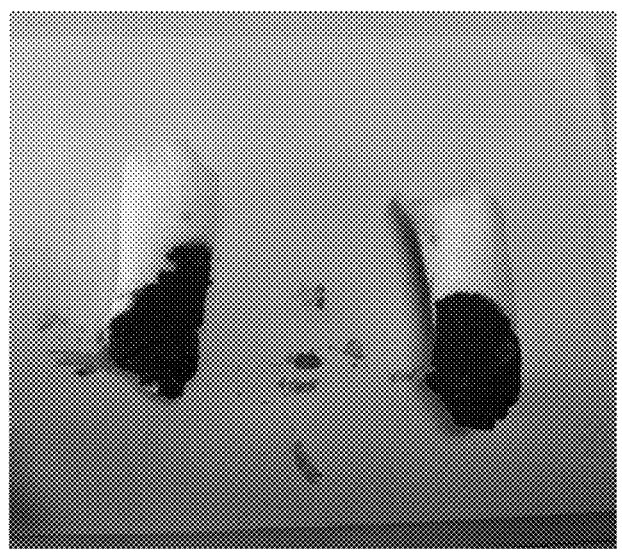
FIG. 11 includes images that show a comparison between a device having an absorbent body with a lysine reservoir shown on the left and a control absorbent body without lysine shows on the right with the dark marker on the non-bloody end.
Figure 11:
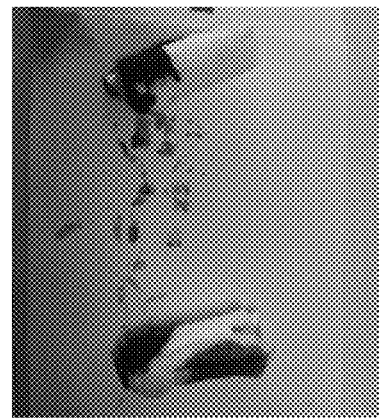

FIG. 11 shows a comparison between a device having an absorbent body with a lysine reservoir shown on the left and a control absorbent body without lysine shows on the right with the dark marker on the non-bloody end. The control absorbent body only absorbed blood but did not slow the blood flow. The test device absorbed blood to the core where the lysine reservoir was located. The device absorbed a lot of blood, but the bleed stopped with the single device in about 1.5 minutes.

Figure 12:
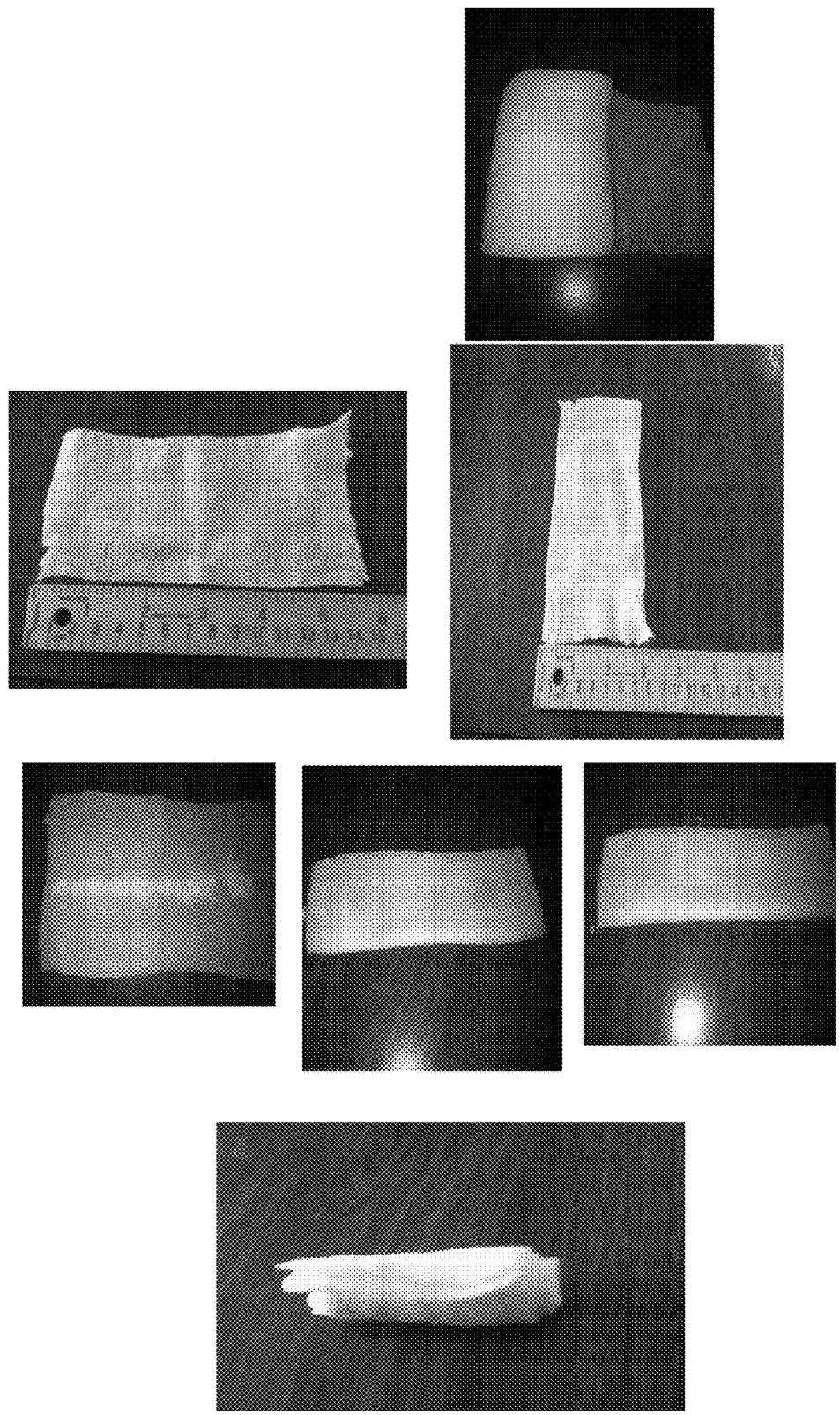
FIG. 12 shows a method of making a device of the invention having a hemostatic composition therein.
Figure 13:
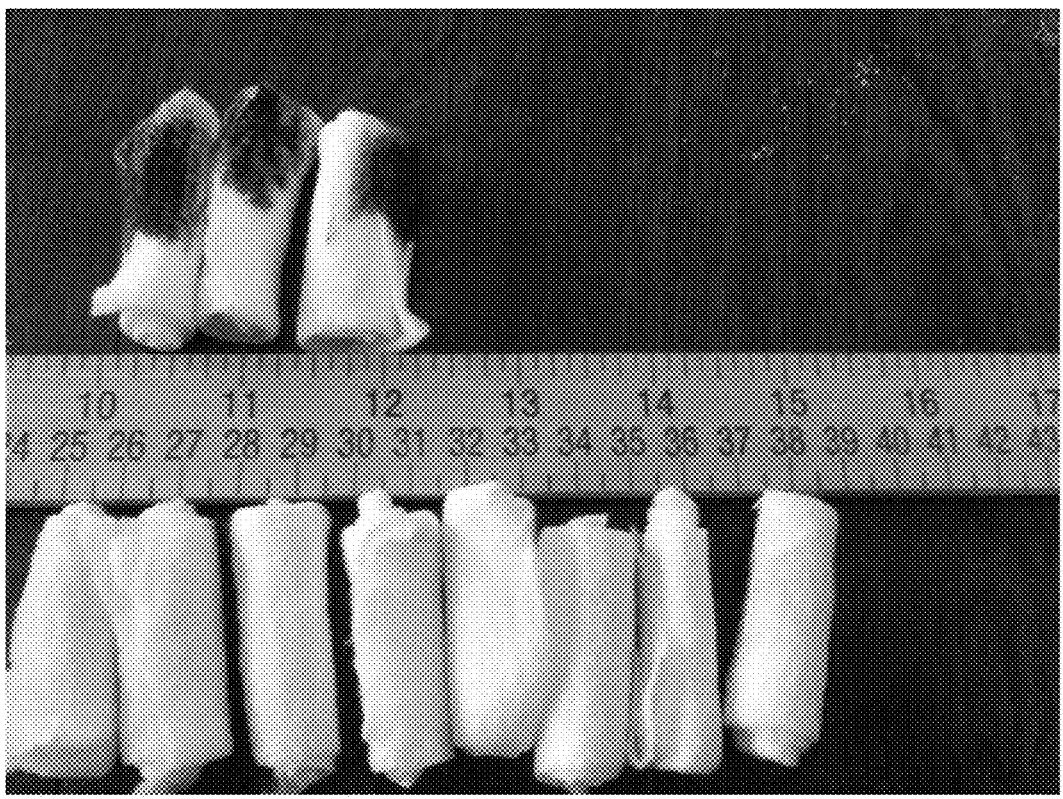
FIG. 13 shows an assortment of control devices (marked with color at end) and devices having the hemostatic composition (all white).

FIG. 12—illustrate an embodiment of a method of making a blood coagulating device with a lysine reservoir. FIG. 12 shows the rolled absorbent gauze material to serve as the body. The gauze is not hemostatic (Walgreens Premium Rolled Gauze—for secure dressings and light absorption. The device is made by: forming an absorptive body to a size and shape of a sheet; placing lysine powder on a surface of the sheet, where the lysine may be anywhere, but shown to be placed along a center crease. Adhesive is used to stick the surface to itself when the substrate is folded at the center crease so that the folded body has the lysine at the fold. The additional adhesive is put on the surface that is showing, and the sheet is rolled into a cylindrical device. The device has the lysine in a multi-layered chamber with the lysine located at one end. FIG. 13 shows a comparison with the lysine-free control devices (marked with the marker at the end opposite of the ruler), and lysine-containing test devices that are all white. The marked end of the controls is not inserted in the nose.

Figure 14:
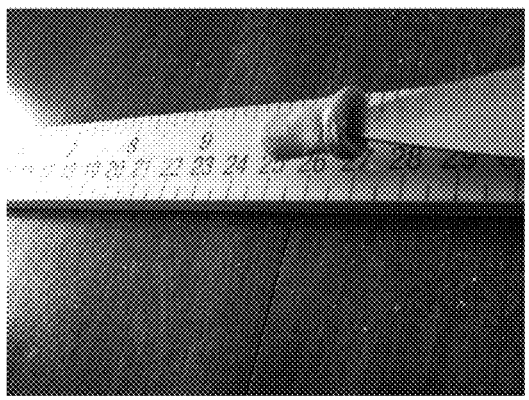
FIG. 14 illustrates a method of making devices having the hemostatic composition and a shape memory member.
Figure 14:
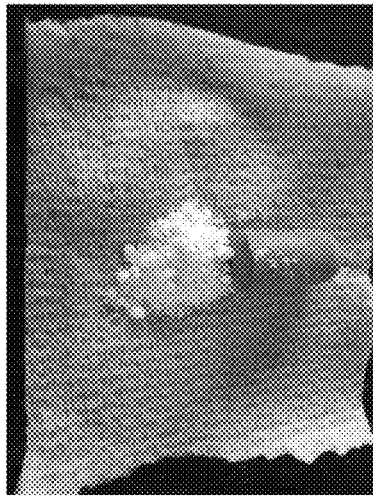
Figure 14:
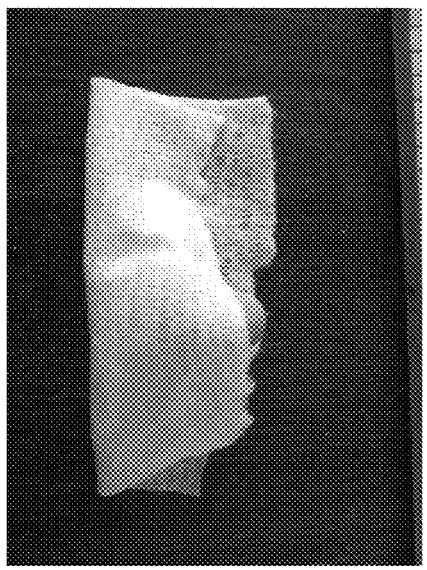
Figure 14:

FIG. 14 shows another embodiment of a method for making a different embodiment of a blood coagulating device. The embodiment includes forming a receptacle in an end of a memory foam device and placing lysine powder in the receptacle. The memory foam and lysine powder is placed in a gauze sheet, and rolled into a cylindrical device.

The invention claimed is:

1. A blood coagulating device comprising:
    an absorbent body adapted to fit in a nasal passageway or vagina; and
    a powdered hemostatic lysine composition associated with the body, the powdered hemostatic lysine composition having an effective amount of lysine amino acid molecules as a hemostatic agent to coagulate blood, wherein the powdered hemostatic lysine composition is associated with the absorbent body such that a first portion of the powdered hemostatic lysine composition contacts the blood upon introduction into the nasal passageway or vagina, the portion of the powdered hemostatic lysine composition being capable of coagulating blood at an interface of the powdered hemostatic lysine composition and blood such that the clot forms and is separable from a second portion of the powdered hemostatic lysine composition upon withdrawal of the blood coagulating device from the nasal passageway or vagina.

2. The device of claim 1, the body comprising a cylindrical or conical member having a first end having the powdered hemostatic lysine composition, the first end being configured for insertion into a nasal passageway or vagina.

3. The device of claim 1, the body being an absorbent hemostatic lysine composition.

4. The device of claim 1, the body comprising a shape memory member, the shape memory member having a first compressed shape and a second expanded shape.

5. The device of claim 1, the body having a chamber having the powdered hemostatic lysine composition.

6. The device of claim 1, the body having a surface having the powdered hemostatic lysine composition.

7. The device of claim 1, the body comprising the powdered hemostatic composition lysine embedded therein.

8. The device of claim 1, the body having one or more depots of the powdered hemostatic lysine composition.

9. The device of claim 1, the body having detachable tab defining at least one side of a chamber having the powdered hemostatic lysine composition.

10. The device of claim 1, the body having a blood-dissolvable portion defining at least one side of a chamber having the powdered hemostatic lysine composition.

11. The device of claim 1, the body having a blood-impermeable member defining at least one side of a chamber having the powdered hemostatic lysine composition, the blood-impermeable member being located at a bottom portion of the body, the bottom portion being opposite of a top portion with respect to the chamber, the top portion being configured to be inserted into a nasal passageway.

12. The device of claim 1, the body containing a blister package, the blister package containing the hemostatic lysine composition.

13. The device of claim 1, the body having an airtight chamber having the hemostatic composition therein.

14. The device of claim 1, the body comprising multiple absorbent body members having the powdered hemostatic lysine composition.

15. The device of claim 1, the body having a blood-absorptive portion and a blood-non-absorptive portion, the powdered hemostatic lysine composition being associated with the blood-absorptive portion.

16. The device of claim 1, wherein the powdered hemostatic lysine composition is in a top region of the absorbent body.

17. The device of claim 1, wherein the powdered hemostatic lysine composition includes the hemostatic agent consisting essentially of lysine amino acid molecules selected from L-lysine, D-lysine, beta lysine, and combinations thereof.

18. The device of claim 1, wherein the powdered hemostatic lysine composition includes L-lysine, D-lysine, and/or beta lysine, and further includes tranexamic acid and/or aminocaproic acid.

19. The device of claim 1, wherein the device is configured with the powdered hemostatic lysine composition positioned on the absorbent body to allow for the second portion of the powdered lysine composition to separate from the clot so as to inhibit rebleeding upon extraction of the device from a nasal passageway.

20. The device of claim 1, wherein the absorbent body is adapted to fit in a nasal passageway.

* * * * *